United States Patent [19]

Andrews et al.

[11] Patent Number: 5,502,183
[45] Date of Patent: Mar. 26, 1996

[54] STEROID INTERMEDIATES AND PROCESSES FOR THEIR PREPARATION

[75] Inventors: David R. Andrews, Maplewood; Anantha R. Sudhakar, East Brunswick, both of N.J.

[73] Assignee: Schering Corporation, Kenilworth, N.J.

[21] Appl. No.: 256,812

[22] PCT Filed: Jan. 26, 1993

[86] PCT No.: PCT/US93/00211

§ 371 Date: Jul. 25, 1994

§ 102(e) Date: Jul. 25, 1994

[87] PCT Pub. No.: WO93/15103

PCT Pub. Date: Aug. 5, 1993

Related U.S. Application Data

[63] Continuation-in-part of Ser. No. 826,695, Jan. 28, 1992, abandoned.

[51] Int. Cl.$^6$ .................................................. C07J 21/00
[52] U.S. Cl. ........................... 540/46; 552/612; 552/616; 552/533; 552/562; 552/566; 552/559; 552/593
[58] Field of Search ................................. 552/612, 616, 552/559, 566, 593, 533, 562; 540/46

*Primary Examiner*—Kimberly J. Kestler
*Attorney, Agent, or Firm*—Paul A. Thompson; Edward H. Mazer

[57] ABSTRACT

Novel steroids having a 9α-hydroxy or a 9α-carbonate substituent can be prepared from 9α-hydroxyandrostenedione and can be utilized in the synthesis of commercially valuable corticosteroids such as betamethasone. The 9α-carbonates are prepared by reaction of the corresponding 9α-hydroxy steroid with a sequence of excess base, trialkylsilyl chloride, alkyl haloformate and alkanol or by using excess base, alkyl haloformate and alkoxide. 9α-Carbonate-17-keto compounds can be treated with lithium acetylide and a lithium salt to afford the corresponding 17α-ethynyl-17β-hydroxy-9α-carbonate. This compound is then esterified with a novel series of reagents to give the 17-ester which can be reduced the corresponding 17-allene. Oxidation of this allene to the bis-epoxide compound, followed by treatment with an alkali metal salt of a carboxylic acid under phase transfer conditions gives the 17α-hydroxy 21-ester 9α-carbonate. Elimination of the 9α-carbonate group affords the a 17α-hydroxy, 9(11)ene, which in a few subsequent steps can be converted to a variety of commercially important corticosteroids. Novel 9α-carbonate compounds are prepared in the various reaction steps.

35 Claims, No Drawings

STEROID INTERMEDIATES AND PROCESSES FOR THEIR PREPARATION

This application is a 371 of PCT/US93/00211 filed Jan. 26,1993 now abandoned and is also a continuation-in-part of U.S. application Ser. No. 07/826,695 filed Jan. 28, 1992 now abandoned.

BACKGROUND OF THE INVENTION

The 9α-hydroxy steroids are known to be useful intermediates for preparing commercially valuable corticosteroids. These corticosteroids such as betamethasone find utility in the treatment of psoriasis, dermatological diseases and inflammation. U.S. Pat. No. 4,127,596 describes a process for dehydrating 9α-hydroxysteroid type compounds with a strong acid (pKa less than 1) to give Δ9,11 steroids. A Δ9,11 steroid is one which possesses a double bond between positions 9 and 11 in the steroid ring.

U.S. Pat. No. 4,102,907 and European Patent Application No. 87201933.6 teach dehydration of steroid intermediates. John Fried and John A. Edwards, *Organic Reactions in Steroid Chemistry*, Vol. II, Van Nostrand Reinhold Co., New York, N.Y. (1972), pp., 382–385; L. F. Fieser and M. Fieser, *Steroids*, Reinhold Publishing Corp., New York (1959), Chapter 18, Homo and Nor Steroids, pp. 577–599 and R. W. Draper and M. S. Puar Carbon-13 Nuclear Magnetic Resonance Spectra of D-homoannulated 17-hydroxypregnan-20-ones, *Steroids* 54/1, July, 1989, pp. 1–10, disclose undesirable D-ring homologation of 17-hydroxy-20-keto steroids by utilizing conventional acidic or alkaline reagents. *J. Org. Chem.*, 44, pp. 1582–1584 (1979) notes that C-9α esters are not readily preparable. The Δ9,11 steroids are useful intermediates for the preparation of pharmaceutically active corticosteroids as taught in L. F. Fieser and M. Fieser, *Steroids*, Chapter 19, Adrenocortical Hormones, pp. 600–726, supra, I. Nitta and H. Ueno, New Synthesis of Corticoids, Yuki Gosei Kagaku, Vol. 45, No. 5 (1987), pp. 445–461, and in J. Redpath and F. J. Zeelen, in *Chem. Soc. Rev.*, Stereoselective Synthesis of Steroid Sidechains, Vol. 12 (1983), pp. 75–98. Thus, it would be desirable to provide a process for preparing Δ9,11 steroids by dehydration of 9α-oxygenated steroids possessing the requisite 17,21-dihydroxy-20-ketone (corticoid) or 17 -hydroxy-20-ketone (pregnane) side chain which avoids D-ring homo-rearrangement and which can also reduce the steps required for their preparation. The present invention utilizes a 9α-carbonate of the 9α-hydroxy steroid as an intermediate in the synthesis of commercially valuable steroids. 9α-carbonates are prepared from the commercially available 9α-hydroxyandrost- 4-ene-3,17-dione or its derivatives by a sequence of either excess base, trialkylsilyl halide, alkyl, vinyl, or phenyl haloformate and alkanol; or a sequence of excess base, excess alkylhaloformate and alkoxide. The use of the 9α-carbonate allows for elimination in the presence of a 17-hydroxy group.

SUMMARY OF THE INVENTION

The present invention is concerned with a process for the preparation of steroid intermediates of the formula

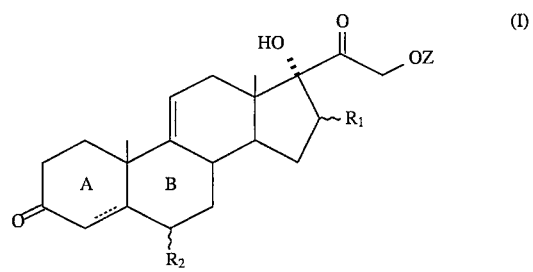

wherein

Z is an acyl group;

R₁ is a hydrogen, α- or β-methyl, hydroxy, or a lower alkoxy group;

R₂ is hydrogen, fluoro, chloro or lower alkyl; and the dotted line represents an optional double bond;

which comprises:

a. optionally contacting a 9α-hydroxy steroid of the formula

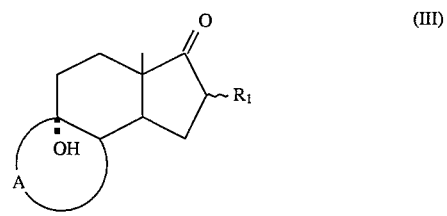

wherein R₁ is as hereinbefore defined and

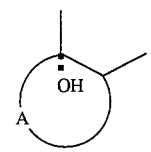

represents i) an enol ether of the formula:

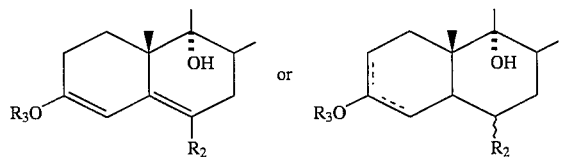

wherein R₃ is a lower alkyl or a trisubstituted silyl group wherein the silyl substituents are independently lower alkyl, phenyl or phenylalkyl; the dashed line represents a double bond present in one or the other position; and R₂ is as hereinbefore defined;

ii) a ketal of the formula:

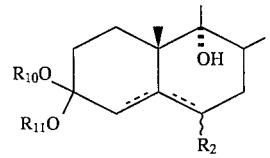

wherein R₁₀ and R₁₁ independently are lower alkyl groups, optionally connected together to form a five or six membered ring; the dashed lines represent an optional bond present in either the A or B ring; and R₂ is as hereinbefore defined; or iii) an enamine of the formula

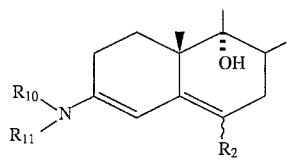

wherein $R_2$, $R_{10}$ and $R_{11}$ are as hereinbefore defined with the proviso that the optional six membered ring may optionally contain an oxygen or nitrogen atom;

with either 1) excess base and a trisubstituted silylchloride;
2) a lower alkyl, vinyl or phenyl haloformate; and
3) a lower alkanol;

or 1) excess base;
2) a lower alkyl, vinyl or phenyl haloformate; and
3) an alkoxide to afford the C-9 carbonate of the formula a)

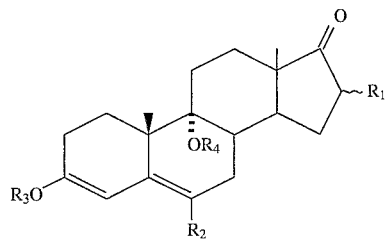
(IVa)

b)

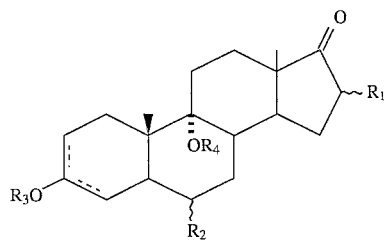
(IVb)

c)

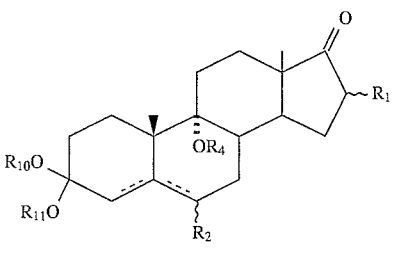
(IVc)

or d)

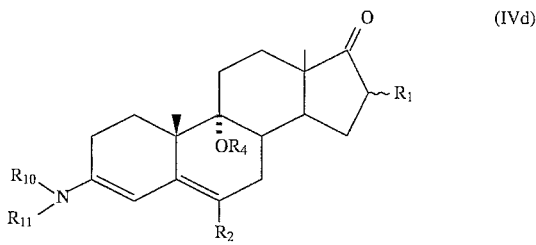
(IVd)

wherein $R_4$ is a lower alkyl, vinyl or phenyl carbonate group, and $R_1$, $R_2$, $R_3$, $R_{10}$ and $R_{11}$ are as hereinbefore defined;

b. contacting the resultant C-9 carbonate of step (a) or the 9α-hydroxy starting material of formula III with lithium acetylide or lithium trimethylsilyl acetylide, optionally in the presence of LiX wherein X is a chloro, bromo or perchlorate ion, to afford the C-17 ethynyl compound of the formula

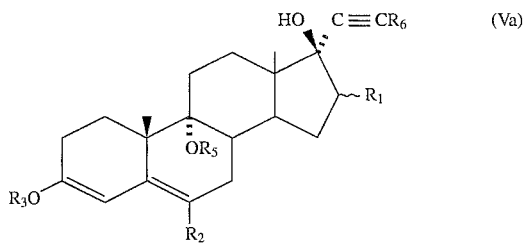
(Va)

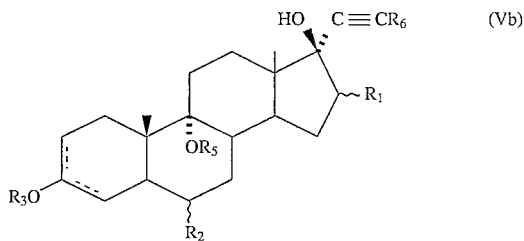
(Vb)

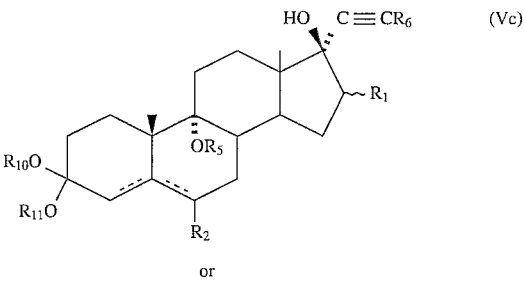
(Vc)

or

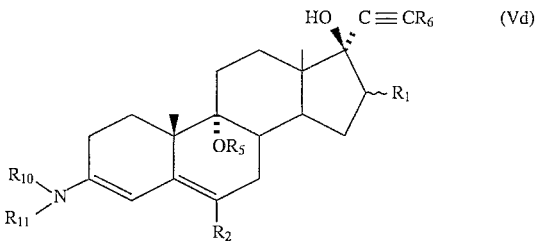
(Vd)

wherein $R_5$ is hydrogen, a lower alkyl carbonate, a vinyl carbonate or a phenyl carbonate group, $R_6$ is hydrogen or a trimethylsilyl group; $R_1, R_2, R_3, R_{10}, R_{11}$ and the dashed and dotted lines are as hereinbefore defined;

c. esterifying the resulting C-17 hydroxyl compound of step b with
  1) catalytic phenoxide formed in situ with a metal hydride and a phenol; and
  2) a diarylcarbonate of the formula

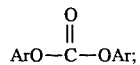

or an alkylaryl carbonate of the formula

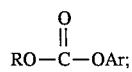

or a diarylcarboxylate of the formula

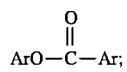

or an arylalkylcarboxylate of the formula

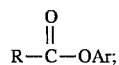

wherein R is a lower alkyl group and Ar is an aryl group; and
  3) a metal hydride; in an aprotic solvent;
to afford the C-17 ester of the formula a)

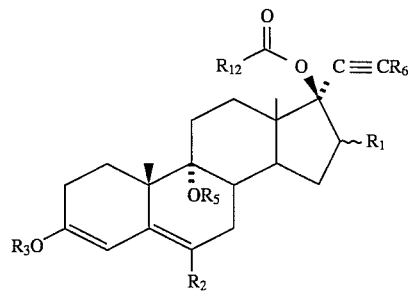
(VIa)

b)

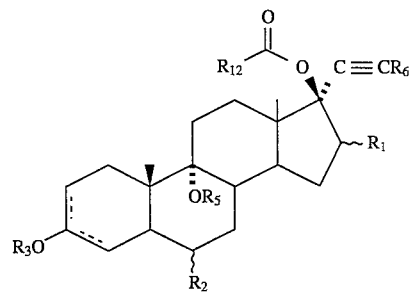
(VIb)

c)

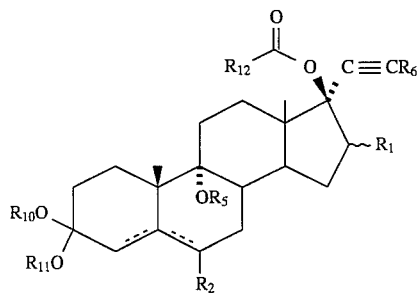
(VIc)

or d)

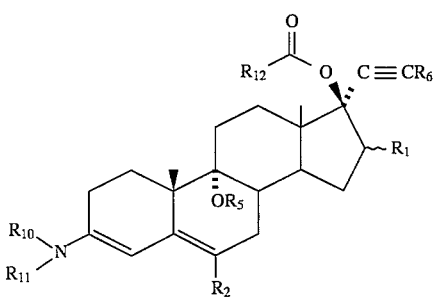
(VId)

wherein $R_{12}$ is a lower alkyl, aryl, lower alkoxy or aryloxy group and $R_1, R_2, R_3, R_5, R_{10}, R_{11}$ and the dashed and dotted lines are as hereinbefore defined; and in the case wherein $R_6$ is a trisubstituted silyl group, removal of that group by a conventional desilylation method;

d. contacting the resulting C-17 ester of step c with one of the following reducing agents:
  1. formic acid or its salts;
  2. a samarium (II) salt such as $SmI_2$;
  3. a transition metal such as Zn;
and a palladium catalyst containing a phosphine or phosphite ligand, to afford the 17-allene of the formula a)

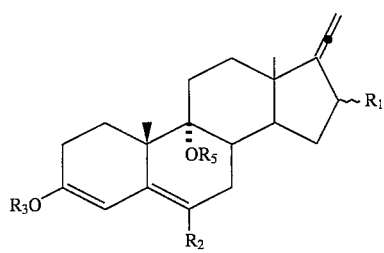
(VIIa)

b)

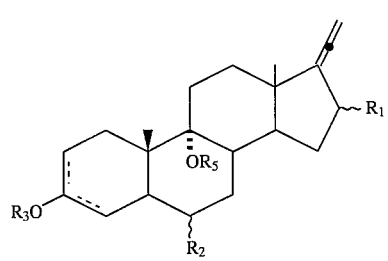
(VIIb)

c)

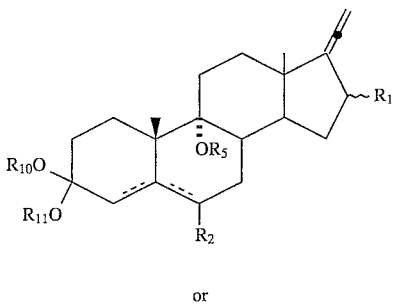
(VIIc)

or d)

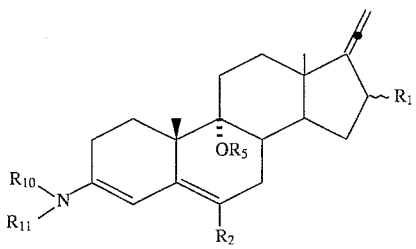
(VIId)

wherein $R_1$, $R_2$, $R_3$, $R_5$, $R_{10}$, $R_{11}$ and the dashed and dotted lines are as hereinbefore defined;

e. treatment of the resulting 17-allene of step d with an aqueous strong acid to afford the 3-one of the formula

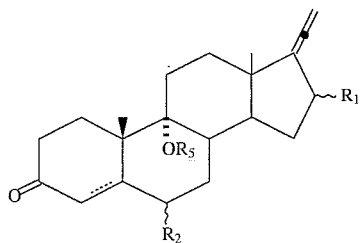
(VIII)

wherein $R_1$, $R_2$, $R_5$ and the dotted line are as hereinbefore defined;

f. oxidizing the resulting 3-one of step e with a dialkyl dioxirane to afford the compound of the formula

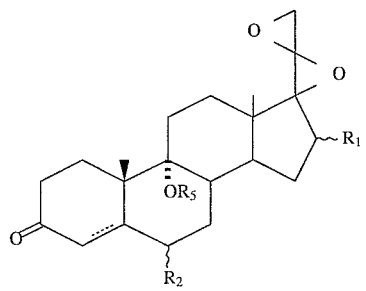
(IX)

wherein $R_1$, $R_2$, $R_5$ and the dotted line are as hereinabove defined;

g. treatment of the compound of step f with an alkali metal salt of a carboxylic acid under phase-transfer conditions to afford the compound of the formula

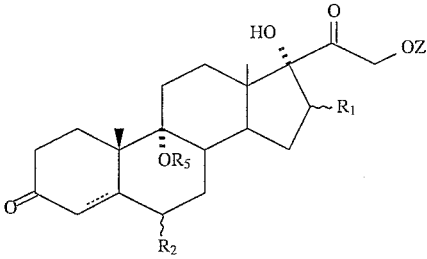
(X)

wherein Z is an acyl group, $R_1$, $R_2$, $R_5$, and the dotted line are as hereinbefore defined; and h. treatment of the compound of step (g) with a strong acid to afford the Δ9,11 steroid of formula I.

DETAILED DESCRIPTION OF THE INVENTION

When utilized in the present Specification and in the appended claims, the terms listed hereinbelow, unless otherwise indicated, are defined as follows:

The wavy line bond, i.e., "∼∼∼" indicates the substituent possesses either the alpha (α) or beta (β) configuration. A substituent possessing the α configuration lies below the plane of the paper, whereas a substituent possessing the β configuration lies above the plane of the paper, as defined in Leland J. Chinn, Paul D. Klimstra, John S. Baran and Raphael Pappo, The Chemistry and Biochemistry of Steroids, Intra-Science Chemistry Reports, Vol. 3, No. 1, Intra-Science Research Foundation, Santa Monica, Calif. (1969), pp. 1–82.

The "⎯⎯⎯" symbol indicates a substituent possessing the β configuration. A dashed line indicates that the substituent possesses the alpha (α) configuration.

The dotted line in conjunction with a solid line, i.e., "⎯⎯⎯", indicates an optional single or double bond.

The term "alkyl" or "lower alkyl" (including the alkyl portion of alkanoyloxy and alkoxy) refers to a straight chain saturated hydrocarbon moiety containing from 1 to 6 carbon atoms, or a branched saturated hydrocarbon moiety of 3 to 7 carbon atoms, such as, for example, methyl (i.e., —CH$_3$), ethyl, propyl, isopropyl, butyl, isobutyl, tert-butyl, pentyl, hexyl and the like.

The term "phenylalkyl" refers to a phenyl moiety covalently bonded to an alkyl moiety of one to six carbon atoms such as, for example, phenylmethyl, 2-phenylethyl and the like.

The term "aryl" refers to phenyl, naphthyl and phenyl substituted by one or more lower alkyl, halo or nitro groups. It is also represented by Ar throughout this specification in various formulae.

The term "acyl" represents a lower alkanoyl group of 2–6 carbons or an aroyl group wherein the aromatic ring or rings are variously substituted with alkyl, halo, nitro, NR$_2$, OR, SR and the like wherein R is independently hydrogen, lower alkyl, cycloalkyl, alkenyl, aryl and acyl, optionally substituted by lower alkyl, halogen or nitro groups.

The term "conventional hydroxy protecting group" refers to any of the well-known standard groups utilized to block the reactivity of the hydroxyl group on asteroid nucleus. Typical of such groups are the carboxylates, carbonates, sulphonates, ether and silyl ether protecting groups. Such groups are typically placed on the hydroxy group prior to reactions wherein the reactivity of the hydroxy group would interfere and cause side reactions, and then removed when the desired reaction has been completed.
The processes of the present invention may be schematically illustrated as follows:
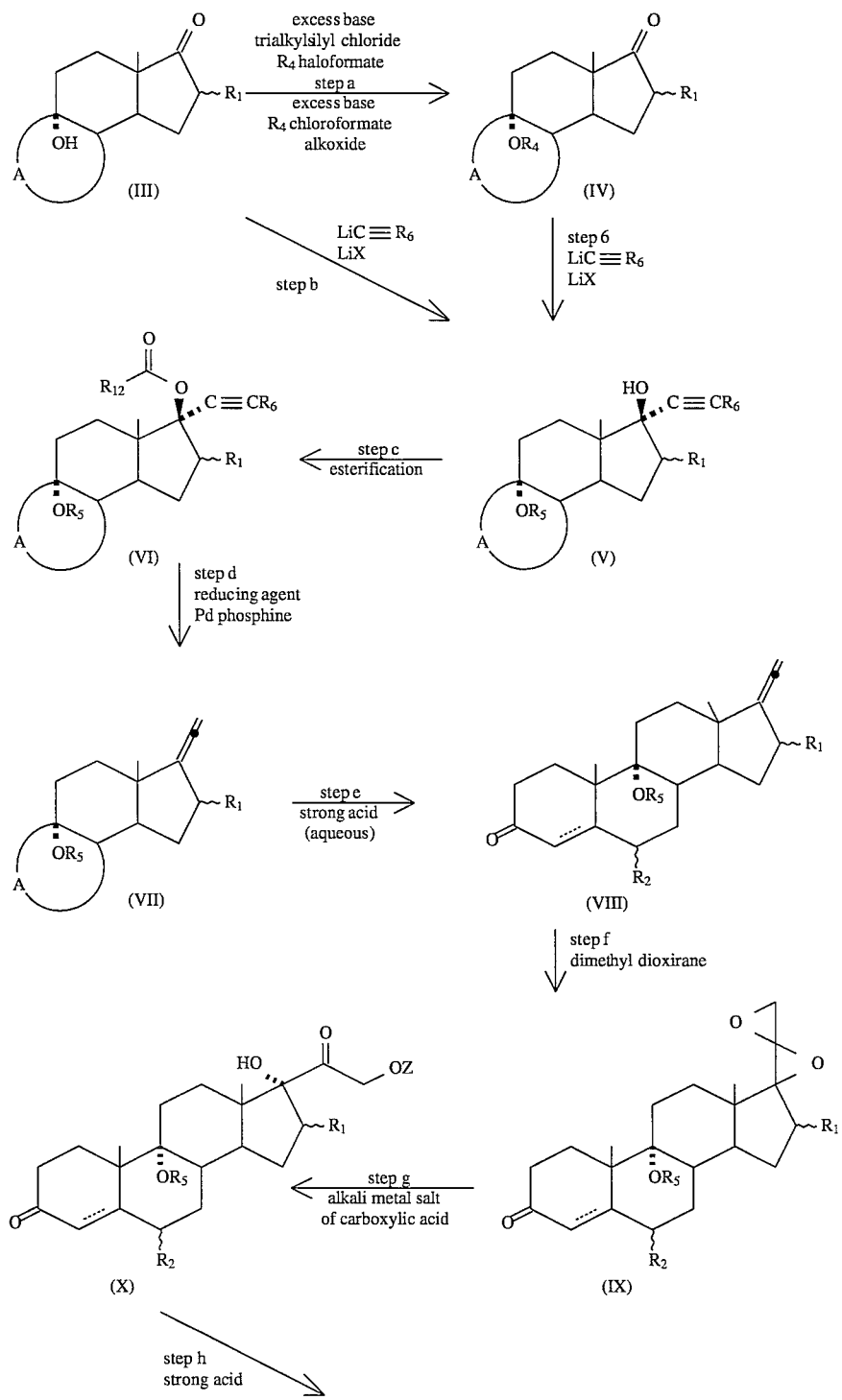

-continued
SCHEME I

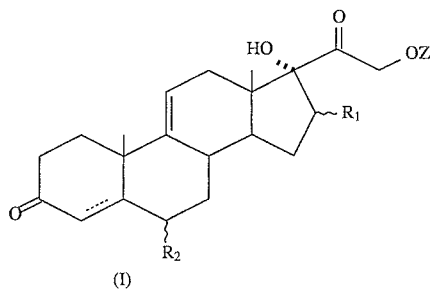

(I)

Compounds of formula III in Scheme I are either known (e.g. N. I. Carruthers, S. Garshasb and A. T. McPhail Journal of Organic Chemistry 1992 57, page 961; N. I. Carruthers, D. R. Andrews, S. Garshasb and R. A. Giusto, J. Chem SOC Perkin I 1992, page 1195) or can be readily prepared by methods known to those skilled in the art. In step a of the process of Scheme I, a 9α-hydroxy steroid of formula III is optionally contacted with excess base and a trialkylsilyl chloride; a lower alkyl, vinyl, or phenyl haloformate; and a lower alkanol to afford a C-9 carbonate of the formulae IVa–IVd. For the conduct of this reaction, the excess base utilized is preferably one such as lithium diisopropylamide or lithium hexamethyl disilazide. Other lithium amide bases my also be utilized as well as sodium or magnesium bases, such as sodium hexamethyl disilazide, sodium hydride or magnesium diisopropyl amide. The, trialkylsilyl chloride utilized is preferably one of the simple alkyl silyl chlorides such as trimethylsilyl chloride, but others known in the art can also be utilized. The lower alkyl, vinyl or phenyl haloformate is preferably a chloroformate, but others such as the bromoformates or carbonic anhydrides (pyrocarbonates) can also be utilized. The lower alkanol utilized in the conduct of this step is preferably methanol, but other lower alkanols such as ethanol, isopropanol, n-propanol and n-butanol can also be used with equal facility. Preferably, this reaction is conducted in an ether solvent, such as tetrahydrofuran, ethyl ether, dimethoxyethane, diethoxymethane, or methyl t-butyl ether. However, toluene and other hydrocarbon solvents are also suitable depending upon the solubility of the particular starting materials chosen.

An alternative route to the 9α-carbonates of formulae IVa–IVd involves the use of an alternate step a wherein the starting material of formula III is treated with excess base and a lower alkyl, vinyl or phenyl haloformate to give an intermediate of the formula

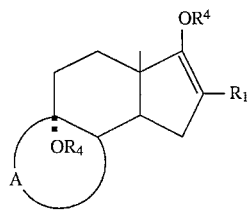

wherein $R_1$ and $R_4$ are as hereinbefore defined, which is then treated with an alkoxide such as sodium methoxide and a lower alkanol such as methanol to afford the intermediate of formulae IVa–IVd.

Step a of the instant process provides a protecting group (the carbonate) for the 9-hydroxy substituent. However, process steps b through h can utilize the 9-hydroxy steroid starting material without the protecting carbonate. This will, however, necessitate an increase in the equivalents of lithium acetylide utilized in step b, i.e., from about 2 equivalents to about 4 equivalents. Due to the expense of this reagent, the optional protection step a makes the overall process much cheaper since only about one-half the amount of lithium acetylide is utilized. The lithium salt is also optional. However, in its absence, the amount of the lithium acetylide utilized must be doubled. Thus, in the case where the 9-carbonate group and lithium salt are utilized, 2 equivalents of the lithium acetylide are necessary. In the case where the 9-carbonate group is present and no lithium salt is used, 4 equivalents of the lithium acetylide are necessary. In the case where no 9-carbonate is used (a 9-hydroxy substituent only), 4 equivalents of lithium acetylide would be necessary in the presence of lithium salt. And, in the case where no 9-carbonate is present and no lithium salt is used, 8 equivalents of the lithium acetylide are necessary. Thus, in the highly preferred embodiment of this invention, both the step a 9-carbonate group and lithium salt are utilized to minimize the use of the expensive lithium acetylide group.

Step b of the instant process contacts the resultant C-9 carbonate of step a with lithium acetylide in the presence of a lithium salt to afford the corresponding C-17 ethynyl compound of the formula Va–Vd. In this step, it is preferable to add at least one equivalent and preferably 2 equivalents of lithium ion prior to contacting the 17-keto steroid with the monolithium acetylide. The lithium ion is added as a lithium salt, for example, lithium chloride, lithium bromide or lithium perchlorate, etc. A preferred salt is lithium chloride.

Generally, slightly more than one equivalent of monolithium acetylide per equivalent of steroid is used. Preferably, about 2 equivalents are utilized in combination with 2 equivalents of lithium salt on a 9-carbonate.

As described above, the amount of lithium acetylide used is dependent upon whether lithium salt and the 9-carbonate substituent are utilized.

Step b of the instant process is preferably conducted at temperatures ranging from –20° to –40° C. in an inert solvent under an inert atmosphere. Particularly suitable solvents are the etheral solvents such as tetrahydrofuran, dioxane, diethyl ether, t-butylmethyl ether, diethoxymethane and dimethoxyethane. The preferred solvent is tetrahydrofuran. Additional details of the process of step b are detailed in European Patent Application No. 0,148,616.

In an alternate embodiment of this step b, a lithium salt of a trisubstituted silyl acetylide is utilized as the ethynylating agent. The resultant compound of formula Va–Vd will thus possess as an $R_6$ substituent, a trisubstituted silyl group. This group is carried intact through process step c and then removed by conventional desilylation methods prior to the compound being subjected to process step d. Typically, removal is accomplished by treatment with a fluoride ion, potassium carbonate in methanol, or silver nitrate.

Step c of the instant process involves esterifying the resulting C-17 hydroxyl compound of formulae Va–Vd produced by step b with a catalytic phenoxide formed in situ with a metal hydride and a phenol; and a diaryl carbonate or an arylalkylcarbonate or an aryl carboxylate in the presence of a metal hydride. This esterification step is preferably conducted in an aprotic solvent such as tetrahydrofuran, ethyl ether, dimethylformamide, dimethyl acetamide or toluene. The selection of the particular diarylcarbonate or alkylarylcarbonate or aryl carboxylate results in the particular $R_{12}$ substituent in the C-17 ester. This reagent may be prepared in situ from the acid chloride and the aryloxide. The metal hydride utilized is preferably sodium hydride, and the hydride is generally utilized in excess of one stoichiometric amount. Certain combinations of reagents in this particular step are preferred. For instance, when diphenylcarbonate is utilized as the esterifying reagent, then sodium hydride and dimethylformamide are utilized therewith. When methylphenylcarbonate is utilized as the esterification reagent, then tetrahydrofuran is preferably utilized as the solvent of choice and sodium hydride as the metal hydride. The reaction is typically conducted at temperatures of about 5° to 50° C. The advantage of this C-17 esterification process is that the side reactions, i.e., undesired acylations and eliminations, are substantially reduced.

Step d of the instant process utilizes the C-17 ester produced by step c to form the 17-allenes of the formula VIIa–VIId. The reduction of the C-17 ester is accomplished utilizing one of a variety of suitable reducing agents. Particularly suitable are formic acid and its salts such as ammonium formate, pyridinium formate and sodium formate. Other equivalent formic acid salts are of equal utility in the practice of this invention. Additional reagents and methods are also described in published Japanese Application No. 60-151,965 [1985]. Other suitable reducing agents are the Samarium (II) salts such as $SmI_2$ and the transition metals such as zinc. The palladium catalyst utilized contains a phosphine or phosphite ligand and includes, but is not limited to, tris (dibenzylidene acetone) dipalladium, palladium diacetate, palladium lactate, palladium benzoate. Typical phosphines are those such as diphenylphosphinoethane, triphenylphosphine, tributyl phosphine, etc. Typical phosphites are triisopropylphosphite and triphenylphosphite. Typically, this reaction is conducted in a solvent such as dimethylformamide, tetrahydrofuran, dioxane, acetonitrile, ethylacetate, methanol, dimethyl sulfoxide, acetone, methylethyl ketone, t-butyl methylether, ethanol, or toluene. Reaction temperatures range from about 0° C. to about 80° C.

Step e of the instant process involves treatment of the resulting 17-allene of formulae VIIa–VIId produced by step d with a strong mineral acid in the presence of water to afford a 3-one of the formula VIII. Alternately, an aqueous mixture of a strong organic acid can also be utilized. Suitable acids are those such as hydrochloric acid or trifluoroacetic acid, sulfuric acid, oxalic and acetic acid. Trifluoroacetic acid is highly preferred in the practice of this invention. Suitable solvents include tetrahydrofuran, methanol, acetone, water, or any combination thereof. Typically, the reaction is conducted at room temperature, but this may vary depending upon the exact nature of the reactants utilized.

Step f of the instant process involves oxidation of the resultant 3-one of formula VIII produced in step e with a dialkyl dioxirane. Typically, this reaction is conducted at temperatures of about −10° to 25° C. in a mixture consisting of water and a suitable solvent such as methylene chloride, dichloroethane, acetone, or toluene. The reagent is typically "dimethyl dioxirane" which may be isolated as a solution in acetone and then contacted with the steroid under anhydrous conditions. More typically, the dimethyl dioxirane reagent is produced in situ by the reaction of Oxone® (a commercially available potassium peroxymonosulfate sold by Aldrich Chemical Corp.) and acetone. Other ketones such as methyl ethyl ketone or other lower alkyl ketones may also be utilized in place of the acetone. Typically, the acceptable pH range for the conduct of this reaction when the reagent is prepared in situ is 6 to 8.5.

Step g of the instant process utilizes the compound of formula IX produced in step f. This compound is treated with an alkaline metal salt of a carboxylic acid under phase transfer conditions to afford the compound of formula X. Typical alkaline metal salts of carboxylic acids are those such as sodium acetate, sodium propionate, sodium benzoate. Typically, the organic solvent utilized is one such as methylene chloride, toluene, ethyl acetate or dimethyl formamide. The phase transfer reagent utilized is typically one such as tetra-n-butylammonium acetate, tetra-n-butylammonium hydrogen sulfate, 18-crown-6 or its derivatives, or another tetra alkyl ammonium salt.

The final step of the instant process (step h) treats the compound produced by step g of formula X with a mineral acid or strong organic acid to afford the desired Δ9,11 steroid. Suitable mineral acids are those such as hydrochloric acid and sulfuric acid. Organic acids, such as methanesulfonic acid and trifluoroacetic acid, may also be utilized. Typical solvents include methylene chloride, trichloromethane, dichloroethane, tetrahydrofuran and water.

A further embodiment of the instant process involves utilizing the compounds of formula IX wherein $R_5$ is an $R_4$ group produced in step f in a reaction with a halide to produce the corresponding compound of the formula

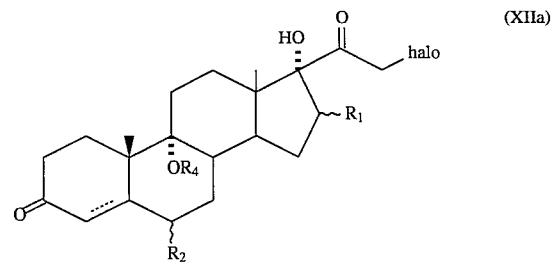

wherein halo is chloro, bromo or iodo and $R_1$, $R_2$ and $R_4$ are as hereinbefore defined; and then subsequently subjecting this compound of formula XIIa to the reaction conditions of steps g and h to afford the resultant Compound of formula I. Additionally, this same reaction can be utilized with compounds of formula XIX (see below) to analogously produce halides of the formula

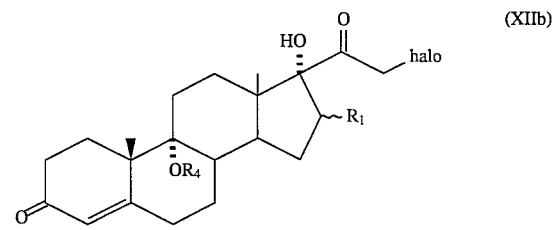

which are then subjected to reaction step g and h to afford the resulting compound of formula II.

In a further alternative embodiment, the reaction conditions of step a can be utilized on compounds of formulae VII and VIII wherein $R_5$ is hydrogen to produce the corresponding compounds of formulae VII and VIII wherein $R_5$ is an alkyl, vinyl or phenylcarbonate. Depending on the particular reactants involved, it may be advantageous to add the 9-carbonate at this step of the reaction sequence.

A highly preferred embodiment of the present invention involves a process for the preparation of steroid intermediates of the formula II. This process is shown in the following Scheme II.

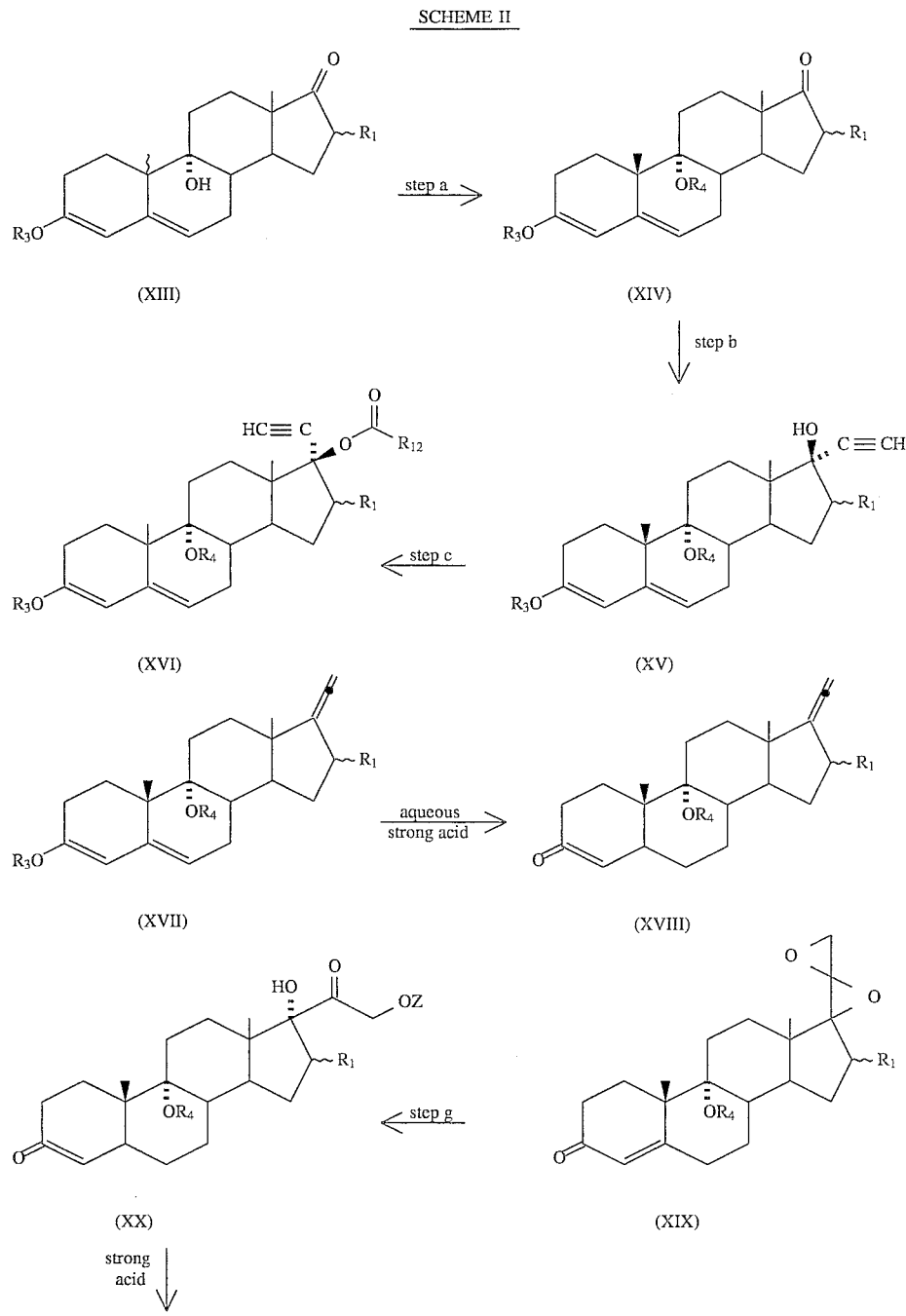

-continued
SCHEME II

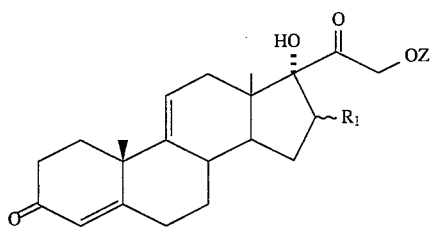

(II)

In Scheme II, the 9α-hydroxy androst-3,5-dien-17-one of formula XIII

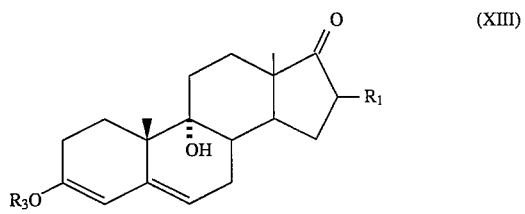

(XIII)

wherein $R_1$ is a hydrogen, α- or β-methyl, hydroxy, or a lower alkoxy group; and $R_3$ is a lower alkyl or a trisubstituted silyl group wherein the silyl substituents are independently lower alkyl, phenyl or phenylalkyl;

is treated as in step a above with excess base and a trialkylsilyl chloride; a lower alkyl vinyl or phenyl haloformate; and a lower alkanol; or excess base; a lower alkyl, vinyl or phenyl haloformate; and an alkoxide; to give the corresponding 9α-carbonate of formula XIV

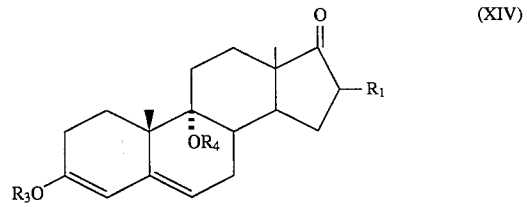

(XIV)

wherein $R_4$ is a lower alkyl, vinyl or phenyl carbonate group, and $R_1$ and $R_3$ are as hereinbefore defined. This 9α-carbonate is then treated as in step b above with lithium acetylide, optionally in the presence of a lithium salt to afford the 17α-ethynyl-9α,17β-dihydroxyandrosta- 3,5-diene 9-carbonate of formula XV. The compound of formula XV is then contacted as in step c above with the desired esterifying reagent so as to provide 17-ester of formula XVI

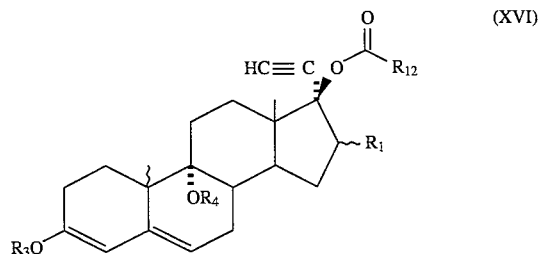

(XVI)

wherein $R_{12}$ is a lower alkyl, aryl, lower alkoxy or aryloxy group and $R_1$, $R_3$ and $R_4$ are as hereinbefore defined. This formula XVI compound is then treated according to step d above with one of the reducing agents, i.e., formic acid or its salts, a samarium II salt; or a transition metal such as zinc; and a palladium catalyst containing a phosphine or phosphite ligand to yield the 9α-hydroxy-17 -vinylideneandrosta-3,5-diene 9α-carbonate of formula XVII. This compound of formula XVII is then treated as in step e above with an aqueous strong acid to yield the 9α-hydroxy-17-vinylidineandrosta- 4-en-3-one 9α-carbonate of formula XVIII. Treatment of this compound of formula XVIII with a dialkyl dioxirane as in step f above affords the 9α-hydroxy-17,20,21 -bis-epoxide-androsta-4-en-3-one 9α-carbonate of formula XIX. This compound of formula XIX is then treated as in step g above with an alkali metal salt of a carboxylic acid under phase transfer conditions to yield the 21-acyloxy-9α, 17α-dihydroxy-pregna- 4-ene-3,20-dione 9α-carbonate of formula XX. Finally, as described above in step h, this compound of formula XX is treated with strong acid to eliminate the 9α-carbonate and yield the desired 21-acyloxy-17α -hydroxy-pregna-4,9(11)-diene-3,20-dione of formula II.

The C-9 carbonates produced by this reaction are novel compounds, heretofore unknown. Consequently, the compounds of formula XIV, XV, XVI, XVII, XVIII, XIX and XX constitute a further embodiment of this invention.

An alternate sequencing of the steps of Scheme I can produce the same compounds of formula I. This alternate sequence is illustrated by Scheme III. In this sequence, the compounds of formula VII (produced by step d of the instant process) having the 9-carbonate substituent ($R_5=R_4$) are subjected to a more vigorous treatment of the hydrolysis of step e to provide the 3 -keto-17-allenes with the Δ9,11 double bond of formula XXI. These more vigorous conditions involve prolonged contact, higher temperature or higher acid concentration. These Δ9,11-3-keto-17-allenes of formula XXI are oxidized according to the reaction conditions of step f to produce the Δ9,11-bis-epoxide compounds of formula XXII. Finally, these compounds of formula XXII are treated according to step g with an alkali metal salt of a carboxylic acid under phase transfer conditions to produce the desired compounds of formula I. In each step in this alternate scheme, the reaction conditions are identical to those utilized for the corresponding 9-hydroxy or 9-carbonate compound except as noted.

SCHEME III

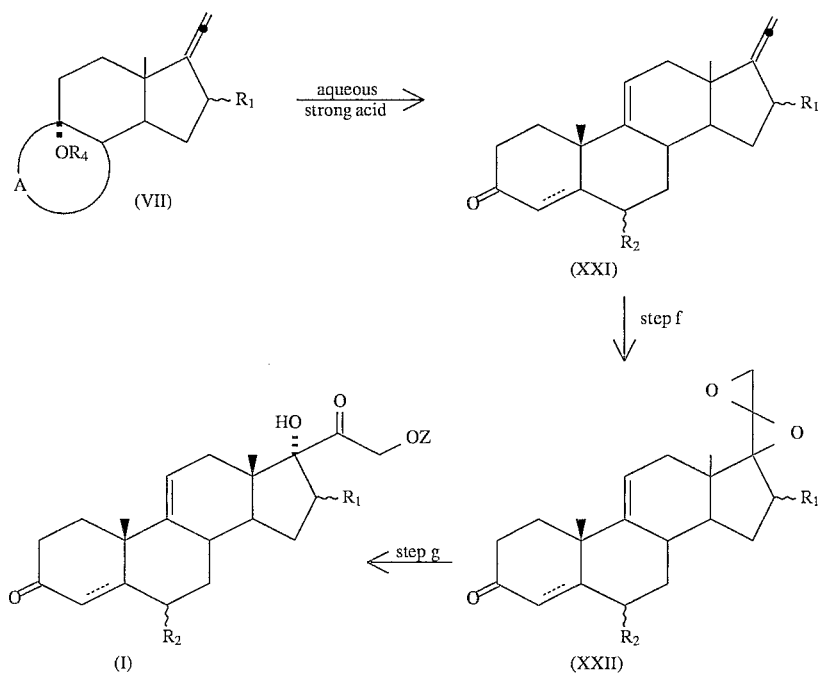

A further embodiment of the present invention is the novel esterification process embodied in step c of Schemes I and II. This process finds special utility in the esterification of alcohols of the formula

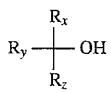  (XXIII)

wherein $R_x$ is an acetylide or trisubstituted silyl acetylide group and $R_y$ and $R_z$ together comprise a steroid ring structure or $R_x$, $R_y$ and $R_z$ are independently alkyl, or substituted alkyl or cycloalkyl optionally containing unsaturation or aryl groups. As exemplified in the schemes and examples herein, this process is particularly useful for producing carbonates and carboxylates of 17-hydroxy steroids under reaction conditions wherein undesirable acylations and eliminations are substantially reduced.

This esterification step is preferably conducted in an aprotic solvent such as tetrahydrofuran, ethyl ether, dimethylformamide, dimethyl acetamide or toluene. The selection of the particular diarylcarbonate or alkylarylcarbonate or aryl carboxylate results in the particular substituent in the ester. This reagent may be prepared in situ from the acid chloride and the phenoxide. The metal hydride utilized is preferably sodium hydride, and the hydride is generally utilized in excess of one stoichiometric amount. Certain combinations of reagents in this particular step are preferred. For instance, when diphenylcarbonate is utilized as the esterifying reagent, then sodium hydride and dimethylformamide are utilized therewith. When methylphenylcarbonate is utilized as the esterification reagent, then tetrahydrofuran is preferably utilized as the solvent of choice and sodium hydride as the metal hydride. The reaction is typically conducted at temperatures of about 5° to 50° C.

Preferred substrates for this reaction of the compounds of formulae V and XV which produce, when treated according to these reaction conditions, the esters of formula VI and XVI.

The following Table 1 includes representative starting materials, reactants and products which exemplify the instant process.

TABLE I

| Starting Material | Esterifying Reagent | Product |
|---|---|---|
| 17α-ethynyl-17β-hydroxy steroid (dienone) | PhOCOCH₃ (O=C) | 17α-ethynyl-17β-(methoxycarbonyloxy) steroid |
| 17α-ethynyl-17β-hydroxy-3-methoxy steroid | PhOCOCH₂CH₃ (O=C) | 17α-ethynyl-17β-(ethoxycarbonyloxy)-3-methoxy steroid |
| 17α-ethynyl-17β-hydroxy-3-methoxy steroid | PhOCOPh (O=C) | 17α-ethynyl-17β-(phenoxycarbonyloxy)-3-methoxy steroid |

TABLE I-continued

| Starting Material | Esterifying Reagent | Product |
|---|---|---|
| (steroid with OH, C≡CH, CH₃, OCH₃, H₃CO groups) | PhOCOPh | (steroid with O-C(=O)-OPh, C≡CH, CH₃, OCH₃, H₃CO groups) |
| (steroid with OH, C≡CH, CH₃, H₃CO groups) | CH₃C₆H₄OCOCH₃ | (steroid with O-C(=O)-OCH₃, C≡CH, CH₃, H₃CO groups) |
| (steroid with OH, C≡CH, CH₃ groups; dienone) | CH₃C₆H₄OCOCH₃ | (steroid with O-C(=O)-OCH₃, C≡CH, CH₃ groups; dienone) |

TABLE I-continued

| Starting Material | Esterifying Reagent | Product |
|---|---|---|
| (steroid with OH, C≡CH, H₃CO-) | PhOCPh (O=) | (steroid with OC(O)Ph, C≡CH, H₃CO-) |
| (steroid with OH, C≡CH, CH₃, H₃CO-) | PhOCPh (O=) | (steroid with OC(O)Ph, C≡CH, CH₃, H₃CO-) |
| (steroid with OH, C≡CH, OCH₃, lactone, H₃CO-) | PhOCCH₃ (O=) | (steroid with OC(O)CH₃, C≡CH, OCH₃, lactone, H₃CO-) |

TABLE I-continued

| Starting Material | Esterifying Reagent | Product |
|---|---|---|
| (17α-ethynyl-3-methoxy-16α-methyl steroid with 17-OH) | PhOCOCH₂CH₃ | (17α-ethynyl-3-methoxy-16α-methyl steroid with 17-OCOEt) |
| (17α-ethynyl-3-oxo steroid with 17-OH) | PhOCOCH₃ | (17α-ethynyl-6-methyl-3-oxo steroid with 17-OCOCH₃) |
| 1-adamantanol | PhOCOCH₃ | 1-adamantyl methyl carbonate (OCOCH₃) |
| (−)-ephedrine (PhCH(OH)CH(CH₃)N(CH₃)₂) | PhOCOCH₃ | ephedrine OCOCH₃ ester |

TABLE I-continued

| Starting Material | Esterifying Reagent | Product |
|---|---|---|
| (methyl glycoside diol with OH and OCH₃ groups) | PhOCOCH₃ | (methyl glycoside with methyl carbonate and OCH₃ groups) |
| H₃C–C(OCH₃)(OH)(OCH₃) | PhOCOCH₃ | H₃C–C(OCH₃)(O–C(=O)–OCH₃)(OCH₃) |
| (bornyl-type OH) | PhOCOCH₃ | (bornyl-type O–C(=O)–OCH₃) |

Ph = phenyl

A still further novel process exemplified in the foregoing schemes is that of steps f and g of Schemes I and II. In this process, compounds of the formula

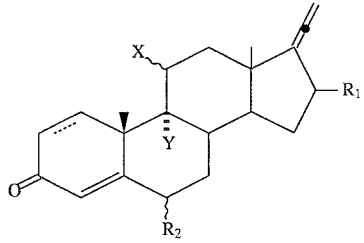

(XXIV)

wherein $R_1$ is a hydrogen, α- or β-methyl hydroxy or a lower alkoxy group;

$R_2$ is hydrogen, fluoro, chloro or lower alkyl;

X is hydrogen, hydroxy or $OR_{13}$;

Y is hydrogen, or when X is hydrogen and there is no 1,2 double bond present, $OR_5$, wherein $R_5$ is hydrogen or a lower alkyl, vinyl or phenylcarbonate group; or X and Y taken together form a 9,11 double bond; $R_{13}$ is a conventional hydroxy protecting group; and the dotted lines represent an optional double bond;

are reacted with dimethyl dioxirane to prepare bis(epoxide) compounds of formula

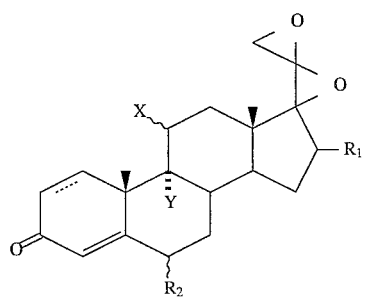

(XXV)

wherein $R_1$, $R_2$, X, Y and the dotted lines are as hereinbefore defined.

This oxidation of the compound of formula XXIV is conducted as described hereinbefore for step f, i.e., with a dialkyl dioxirane. Typically, this reaction is conducted at temperatures of about −10° to 25° C. in a suitable solvent such as methylene chloride, dichloroethane, acetone, or toluene. The reagent is typically "dimethyl dioxirane" which may be isolated as a solution in acetone and then contacted with the steroid under anhydrous conditions. More typically, the dimethyl dioxirane reagent is produced in situ by the reaction of Oxone® and acetone. Other ketones such as methyl ethyl ketone or other lower alkyl ketones may also be utilized in place of the acetone. Typically, the acceptable pH range for the conduct of this reaction when the reagent is prepared in situ is 6 to 8.5.

These bis(epoxides) of formula XXV are then reacted with suitable nucleophilic reagents to give compounds of the formula

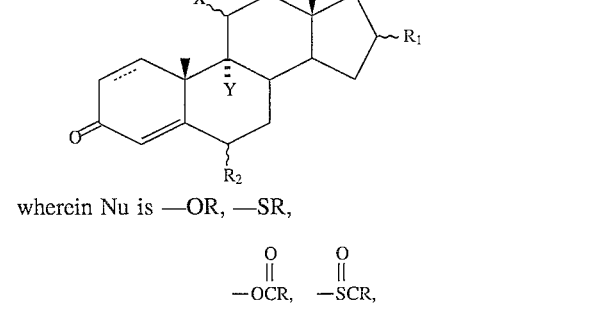

(XXVI)

wherein Nu is —OR, —SR,

halogen,

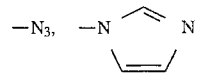

—NRR, —SCN, —CN, —SO$_2$R, —N(R)NRR, —N(R)OR or —ONRR; wherein R is independently hydrogen, lower alkyl, cycloalkyl, alkenyl, aryl, optionally substituted by lower alkyl, halogen or nitro groups; and $R_1$, $R_2$, X, Y, and the dotted lines are as hereinbefore defined.

When salts of

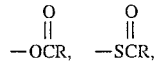

—N$_3$, —CN, halogen, —SCN, and —SO$_2$R are used, the reaction is best performed in a two-phase, water-organic solvent mixture in the presence of a phase transfer catalyst. Typical organic solvents are ethyl acetate, dichloromethane, toluene, heptane, and methyl t-butyl ether. Typical phase-transfer agents are tetra-alkyl ammonium salts, e.g., tetrabutylammonium hydrogen sulphate, benzyltriethylammonium chloride; crown ethers, e.g., 18-crown-6 and the like. A typical temperature range is from about 5° to 50° C.

With non-ionic reagents, for example, amines, hydrazines, hydroxylamines and imidazole, the reaction is best performed in an organic solvent. Typical solvents are dimethylformamide, dimethyl sulfoxide, tetrahydrofuran, methyl-t-butyl ether, toluene, methylenechloride, chloroform and methanol. A typical temperature range is from about 5°–50° C.

As exemplified by the various schemes and examples herein, this process provides an elegant method of producing a wide variety of 21-substituted-20-keto-17-hydroxysteroids which are useful intermediates in many syntheses. Since the reaction conditions are mild, the side reactions are either reduced or greatly eliminated, thus producing intermediates in almost quantitative yields.

Preferred substrates for this reaction are compounds of formulae VIII and XVIII which produce the intermediates of formulae IX and XIX, and ultimately the desired compounds of formulae X and XX when treated according to these reaction conditions. Table II, below, gives representative substrates, reagents and products exemplary of this process.

TABLE II
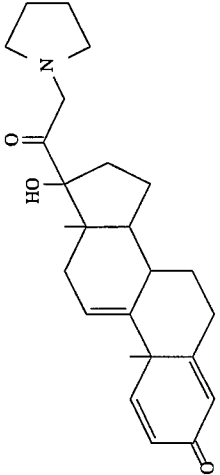

TABLE II-continued

| Starting Material | Nucleophilic Reagent | Product |
|---|---|---|
| (spiroepoxide steroid with 6α-TBDMSO, 16β-CH₃, 1,4-dien-3-one) | PhS(O)—ONa (phase transfer conditions) | 21-(phenylsulfonyl)-17-hydroxy steroid with 6α-TBDMSO, 16β-CH₃, 1,4-dien-3-one |
| (spiroepoxide steroid with 11β-OH, 16β-CH₃, 4-en-3-one) | AcSK (phase transfer conditions) | 21-SAc-17-hydroxy steroid with 11β-OH, 16β-CH₃, 4-en-3-one |
| (spiroepoxide steroid with 7α,15α-lactone bridge, 16β-CH₃, OCH₃, 4-en-3-one) | imidazole / H (CDCl₃) | 21-(imidazol-1-yl)-17-hydroxy steroid with lactone, 16β-CH₃, OCH₃, 4-en-3-one |
| (spiroepoxide steroid with lactone, 16β-CH₃, OCH₃, 4-en-3-one) | NaBr (phase transfer conditions) | 21-bromo-17-hydroxy steroid with lactone, 16β-CH₃, OCH₃, 4-en-3-one |

TABLE II-continued

| Starting Material | Nucleophilic Reagent | Product |
|---|---|---|
| (epoxide steroid) | NaOCH₃ (methanol) → | (steroid with –C(O)CH₂OCH₃ side chain) |
| (epoxide steroid) | NaCN (phase transfer conditions) → | (steroid with –C(O)CH₂CN side chain) |
| (epoxide steroid) | PhSNa (tetrahydrofuran) → | (steroid with –C(O)CH₂SPh side chain) |

A yet further novel process step utilized in the instant process is that of step h of Schemes I and II for compounds of formula XXVIIa and the alternate sequencing described on page 25 herein for compounds of formula XXVIIa and XXVIIb. Compounds of formulae XXVIIa or XXVIIb:

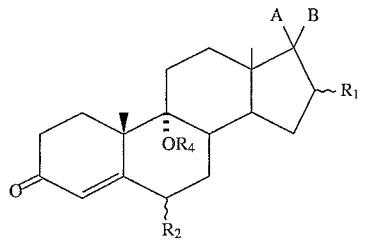
(XXVIIa)

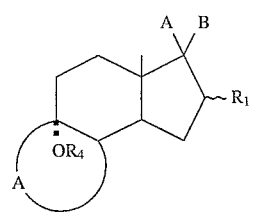
(XXVIIb)

wherein A and B together are keto, ketal, allene,

$=CHCOR_{13}$;

or $=CHCH_2OR_{13}$, or

A is hydrogen, lower alkyl, lower alkynyl, lower alkenyl aryl or alkylaryl —CN,

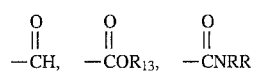

or —COCH$_2$W;

B is hydrogen, OH, OR$_{13}$, or together with carbon-16 forms a 16,17-double bond or a 16,17-epoxide;

R$_1$ is hydrogen, α- or β-methyl, hydroxy or lower alkoxy;

R$_2$ is hydrogen, fluoro, chloro or lower alkyl;

R$_4$ is a lower alkyl, vinyl or phenyl carbonate group;

W is hydrogen, lower alkyl, lower alkenyl, lower alkynyl aryl or alkylaryl; —OR, —SR,

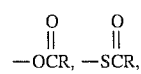

halogen, —N$_3$,

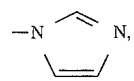

—NRR, —SCN, —CN, —SO$_2$R, —N(R)NRR, —N(R)OR or —ONRR;

R is independently hydrogen, lower alkyl, cycloalkyl, alkenyl, aryl, optionally substituted by lower alkyl, halogen or nitro groups;

R$_{13}$ is a conventional hydroxy protecting group; and

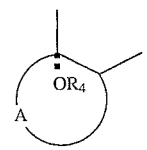

represents i) an enol ether of the formula:

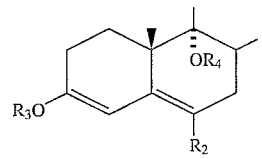

or

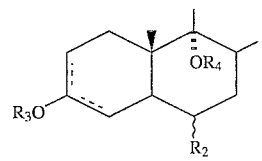

wherein R$_3$ is a lower alkyl or a trisubstituted silyl group wherein the silyl substituents are independently lower alkyl, phenyl or phenylalkyl; the dashed line represents a double bond present in one or the other position; and R$_2$ and R$_4$ is as hereinbefore defined;

ii) a ketal of the formula:

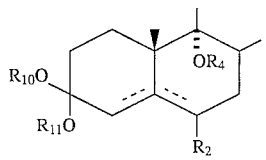

wherein R$_{10}$ and R$_{11}$ independently are lower alkyl groups, optionally connected together to form a ring which optionally may contain an oxygen or nitrogen atom; the dashed lines represent an optional bond present in either the A or B ring;

iii) an enamine of the formula

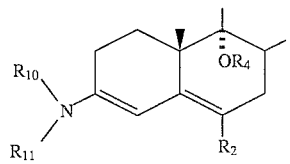

wherein R$_2$, R$_4$, R$_{10}$ and R$_{11}$ are as hereinbefore defined;

are treated with a strong acid to generate the Δ9(11) enes of formula XXVIII

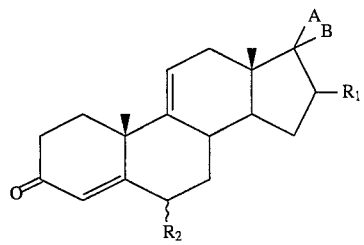

(XXVIII)

wherein A, B, $R_1$ and $R_2$ are as hereinbefore defined.

When the compounds of formula XXVIIa are utilized as starting material, the elimination is conducted under either aqueous or anhydrous conditions. When the compounds of formula XXVIIb are utilized as starting material, an aqueous strong acid must be utilized.

Suitable mineral acids are those such as hydrochloric acid and sulfuric acid. Organic acids, such as methanesulfonic acid and trifluoroacetic acid, may also be utilized. Typical solvents include methylene chloride, trichloromethane, dichloroethane, tetrahydrofuran and water.

Preferred substrates for this reaction are the compounds of formulae X and XX which produce, when treated according to these reaction conditions, the corresponding compounds of formulae I and II. Table III below illustrates representative substrates, reagents and products exemplary of this process.

TABLE III

| Starting Material | Strong Acid | Product |
|---|---|---|
| | aqueous HCl / tetrahydrofuran | |
| | trichloroacetic acid / methylene chloride | |
| | trifluoroacetic acid / CDCl₃ | |
| | aqueous HCl / tetrahydrofuran | |

TABLE III-continued

| Starting Material | Strong Acid | Product |
|---|---|---|
| (steroid with 17α-OH, 17β-CH₃, 21-Br ketone, and lactone bridge, 4-en-3-one) | trifluoroacetic acid → methylene chloride | (steroid with 17α-OH, 17β-CH₃, 21-Br ketone, 4,6-dien-3-one) |
| (steroid with 17β-CH₃, 17-exomethylene, OCH=CH₂, lactone bridge, 3-methoxy-diene) | aqueous HCl → tetrahydrofuran | (steroid with 17β-CH₃, 17-exomethylene, 4-en-3-one) |
| (steroid with 17α-OH, 17β-CH₃, 17-C≡C-TMS, lactone bridge, 3-methoxy-diene) | aqueous HCl → tetrahydrofuran | (steroid with 17α-OH, 17β-CH₃, 17-C≡C-TMS, 4,6-dien-3-one) |
| (steroid with 17-OH, 17β-CH₃, 21-imidazolyl ketone, lactone bridge, 4-en-3-one) | trifluoroacetic acid → methylene chloride | (steroid with 17-OH, 17β-CH₃, 21-imidazolyl ketone, 4,6-dien-3-one) |

TABLE III-continued

| Starting Material | Strong Acid | Product |
|---|---|---|
| [steroid with 11,17-lactone bridge, 17-OH, 21-OCH₃, 16-CH₃, 6-OCH₃] | trifluoroacetic acid / methylene chloride → | [pregn-4-ene-3,20-dione with 17-OH, 21-OCH₃, 16-CH₃] |
| [steroid with 11,17-lactone bridge, 17-OH, 21-SPh, 16-CH₃, 6-OCH₃] | trifluoroacetic acid / methylene chloride → | [pregna-4,6-diene-3,20-dione with 17-OH, 21-SPh, 16-CH₃] |

The following examples illustrate various embodiments by which the present invention can be practiced, but as such, should not be limited to the overall scope of the same. All temperatures are in degrees Celsius (°C.).

EXAMPLE A

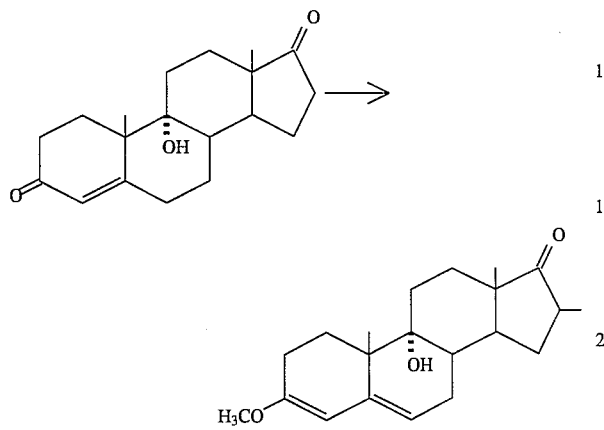

9α-hydroxyandrost-4-ene-3,17-dione (100 g, 0.324 mol) was added to 450 mls tetrahydrofuran. To the resulting mixture, trimethyl orthoformate (105 ml, 0.97 mol) and (+/−) camphor sulfonic acid (3.5 g, 0.015 mol) was added. The mixture was then stirred at 20°–25° C. for 4 hours under nitrogen. Triethylamine (2.2 ml, 0.015 mol) was added to neutralize the camphor sulfonic acid. The reaction mixture was concentrated under vacuum (27–28 inches Hg.) at 5°–10° C. to 250 mls. and cooled to 0°–5° C. Sodium methoxide (26 g, 0.48 mol) was added over 20 minutes at 0°–5° C. Diethyl oxalate (53 ml, 0.39 mol) was added over 20 minutes at 0°–5° C. The mixture was agitated at 20°–25° C. over 16 hours under nitrogen. The mixture was then charged to a 1 liter glass autoclave and sodium iodide (24.3 g, 0.162 mol) added. The autoclave was purged with nitrogen three times and charged with methyl chloride (30–35 g, 0.62–0.71 mol). The contents of the autoclave were then heated to 60°– 65° C. with agitation and maintained at this temperature for 16 hours. The mixture was cooled to 20°–25° C. and transferred to a 2 liter 3 neck flask. Tetrahydrofuran was displaced with 1.2 liters methanol under vacuum (27– 28 in. Hg) at 10°–15° C. The resulting mixture was cooled to 0°–5° C. and sodium methoxide (52.5 g, 0.97 mol) was added over 30–40 minutes. The mixture was stirred at 0°– 5° C. for about 16 hours under nitrogen. Methanol was displaced under vacuum (27–28 in Hg.) with 600 mls water at 0°–10° C. The mixture was cooled to 0°–5° C. and acidified to pH=8.0 with acetic acid (182 ml, 3.2 mol). The mixture was added to 10 liters 0°–5° C. water with stirring over 15 minutes. The precipitate was then filtered and washed with water (2×500 ml). Then the cake was dried in a vacuum oven at 35°–40° C. under a nitrogen bleed to constant weight to give 9α-hydroxy-3 -methoxy-16β-methylandrost-3,5-dien-17-one (87–88 g, 81%).

EXAMPLE 1A

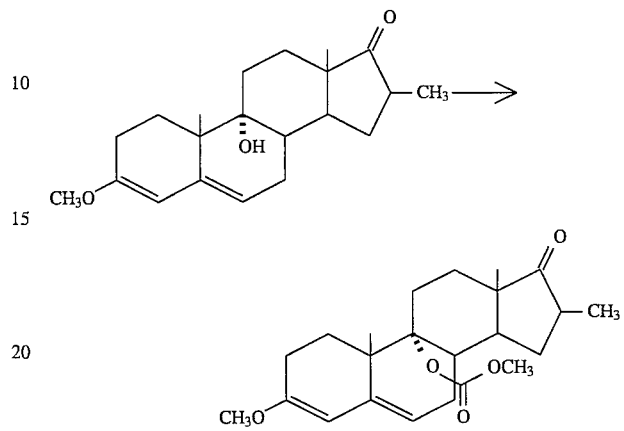

The compound prepared by Example A (20 g, 0.06 mol) was added to 50 mls. tetrahydrofuran. The mixture was cooled to −20° C. under nitrogen. To the resulting slurry, lithium hexamethyl disilazide (1.0M in tetrahydrofuran, 180 ml, 0.18 mol) was added over 30 minutes at −20° C. The resulting mixture was then agitated for 30 minutes at −20° C. Trimethylsilyl chloride (8.5 ml, 0.066 mol) was added at −20° C. over 5– 10 minutes. The mixture was agitated for 50 minutes at −20° C. Then, methyl chloroformate (7.0 ml, 0.09 mol) was added at −20° C. over 5–10 minutes and the mixture stirred at −20° C. for 110 minutes. Additional methyl chloroformate (0.9 ml, 0.012 mol) was added at −20° C. over 5 minutes. The mixture was agitated for 60 minutes at −20° C. 50 mls methanol was added at −20° C. to quench the reaction and tetrahydrofuran was displaced with 0.5 liters methanol under vacuum (27–28 in. Hg) at 0°–10° C. The resulting mixture was agitated for 16 hours at 20°– 25° C. under nitrogen and acidified to pH=8.0 with acetic acid (2.0 ml, 0.036 mol) at 20°–25° C. Methanol was displaced under vacuum (27–28 in Hg.) with 250 mls water at 15°–20° C. The resulting mixture was filtered and washed with water (3×100 ml). The cake was dried in a vacuum oven at 35°–40° C. under a nitrogen bleed to constant weight to give 9α-hydroxy-3-methoxy- 16β-methylandrost-3,5-dien-17-one 9α-methylcarbonate (21–22 g, 90%).

EXAMPLE 1B

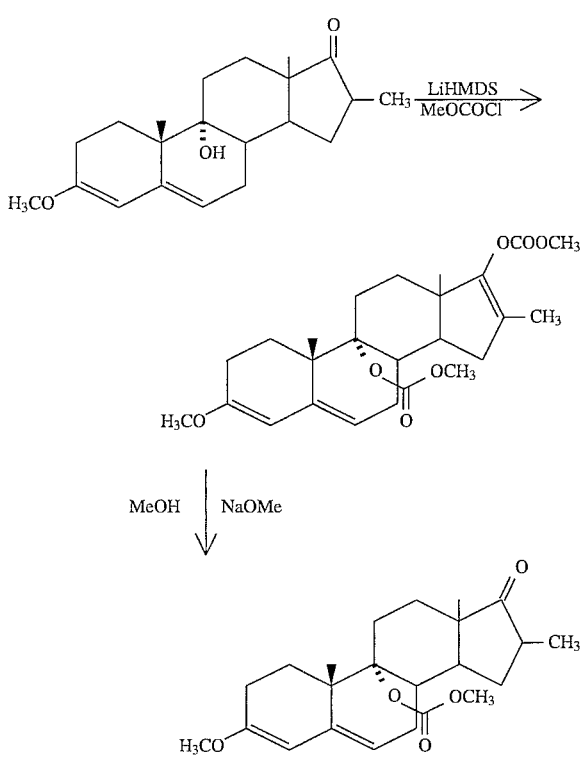

To a solution of 10 grams 9α-hydroxy-3-methoxy-16β-methylandrost-3,5-dien-17-dione in 25 ml tetrahydrofuran under nitrogen was added 80 ml (3.0 equivalents) 1.0 LiHMDS in tetrahydrofuran at 20° C. over a 20–25 minute period. The resulting orange-red solution was stirred for 30 minutes at −20° C. and then 5.5 ml (2.75 equivalents) of previously dried methyl chloroformate was added. The resulting mixture was then stirred at −20° C. for 140 minutes whereupon 30 ml of methanol was added while allowing the mixture to warm to 20° C. The tetrahydrofuran was removed by vacuum distillation and replaced with 250 ml methanol at constant volume (110 ml). Then, 2.8 grams (2.0 equivalents) sodium methoxide was added and the resultant slurry stirred upon nitrogen for about 18 hours. Then, 3.5 ml acetic acid was added (to pH=8.0), the methanol was removed by vacuum and replaced with 100 ml deionized water at constant volume over 2–3 hours. The resulting mixture was then precipitated by its addition to 1000 ml 0°–5° C. water in a flask with agitation. The mixture was stirred for 15–20 minutes and then filtered. The cake was washed twice with 50 ml portions of deionized water and dried in a vacuum over at 35°–40° under nitrogen to constant weight to afford 9α-hydroxy-3-methoxy-16β-methylandrost-3,5 -diene-17-one 9α-methylcarbonate (10.66 grams).

EXAMPLE 2A

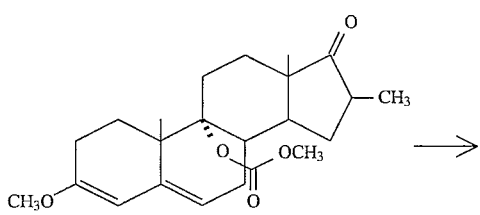

-continued

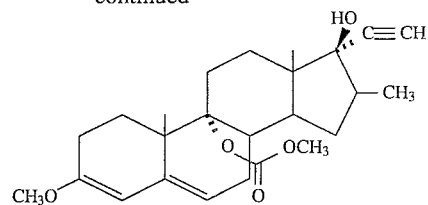

This example was performed under an inert atmosphere. A solution of lithium diisopropylamide prepared by the addition of n-butyllithium (125 ml, 2.5M in hexane)) to diisopropylamine (40 ml) in tetrahydrofuran (100 ml) maintained at −20° C. was slowly added to a saturated solution of acetylene in tetrahydrofuran (375 ml) maintained at −40° C. containing lithium chloride (11 g). The mixture was stirred for about 20 minutes after which 50 g of the compound prepared in Example 1A was added. The mixture was agitated for about 1 hour while warming to −20° C. after which 50 ml acetone was added and the cooling bath removed. The organic solvents were removed by vacuum distillation and concomitantly replaced with a mixture of 25 ml concentrated HCl in 750 ml water. The pH of the resulting slurry was carefully adjusted to pH= 4 with approximately 10 ml acetic acid and the mixture added to 5 L ice water with vigorous agitation. The solid product was collected by filtration, washed with water until neutral and dried in a vacuum oven at 40° C. under a nitrogen bleed to constant weight, to produce 52 g 17α-ethynyl-9α,17β-dihydroxy-3-methoxy-16β -methylandrosta-3,5-diene 9-methylcarbonate.

EXAMPLE 2B

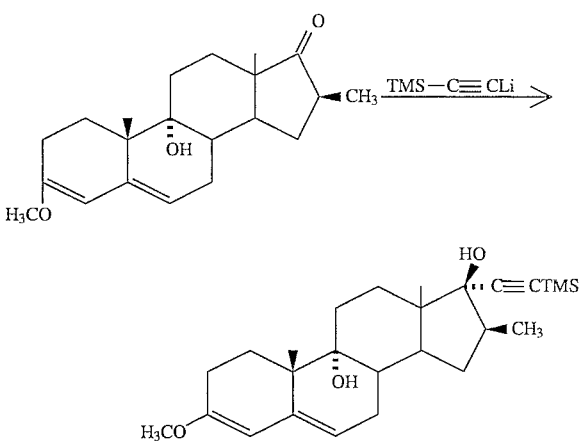

To a solution of trimethylsilyl acetylene (25 g) in 100 ml tetrahydrofuran at −78° C., n-butyl lithium (150 ml, 1.6M) was added. The mixture was stirred at −70° C. for 15 minutes, at 0° C. for 30 minutes, cooled to −70° C., and 9α-hydroxy-3-methoxy-16β-methylandrost-3,5-dien-17-one was added. After 30 minutes at −70° C., the mixture was placed in an ice water bath and stirred overnight. The mixture was then quenched by adding ice cold water and extracted with ethyl acetate. The organic layer was separated, dried and evaporated to afford a brown oil. Chromatography (twice) on silica gel gave, as a yellow oil, 10 grams of 17α-trimethylsilylethynyl-9α,17β -dihydroxy-3-methoxy-16β-methylandrosta-3,5-diene.

EXAMPLE 3A

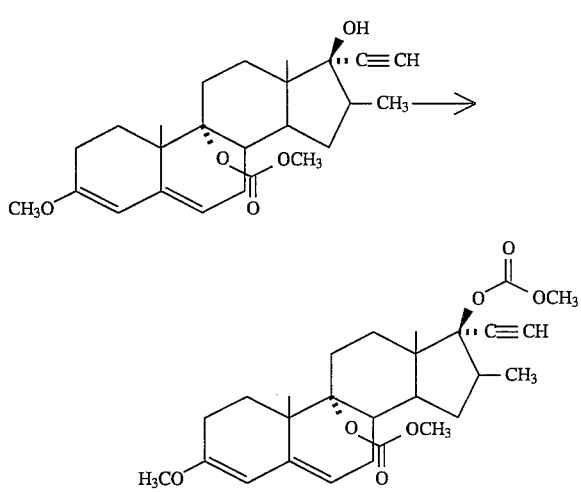

0.95 sodium hydride (60% in oil) was washed with 10 ml hexane and the organic solvent carefully decanted. 10 ml tetrahydrofuran and 2.5 ml methylphenylcarbonate was added and the mixture cooled to 0°–5° C. 5 g of the compound prepared in Example 2A was added, the cooling bath removed, and the reaction stirred overnight at room temperature. The solution was again cooled to 0°–5° C. and quenched by the careful addition of 2 ml propionic acid in 3.5 ml tetrahydrofuran. The solvents were removed by vacuum distillation and 100 ml methanol added. The methanol was removed by vacuum distillation and 20 ml water was added. The mixture was cooled to 0°–5° C., the solids filtered, washed with water until neutral and dried to constant weight to give 5.6 g 17α-ethynyl- 9α,17β-dihydroxy-3-methoxy-16β-methylandrosta-3,5-diene 9,17-bis(methylcarbonate).

EXAMPLE 3B

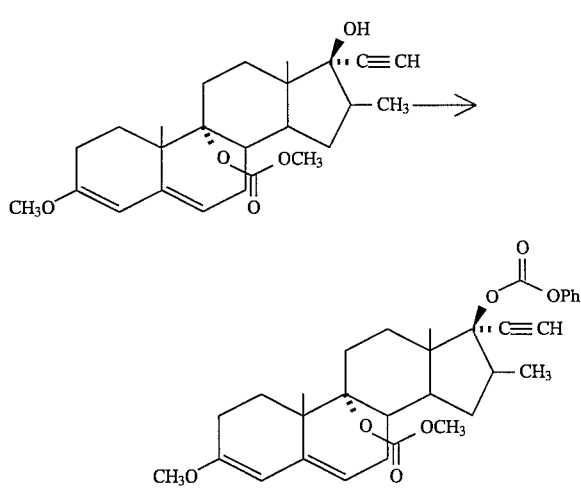

To a solution cooled to 0°–5° C. of 4 g diphenylcarbonate in 4 ml dimethylformamide was added 600 mg sodium hydride (60% in oil) followed by 2.0 g of the product of Example 2. After degassing, the mixture was heated to 40° C. and stirred for 24 hours. Then, 4 ml tetrahydrofuran was added, the solution again cooled to 0°–5° C. and 4 ml water slowly added. The solution was allowed to come to room temperature and 20 ml methyl-t-butyl ether and 20 ml water was added. The organic layer was separated, washed with aqueous sodium hydroxide and the solvents removed by evaporation to afford as product 17α-ethynyl-9α,17β-dihydroxy-3 -methoxy-16β-methylandrosta-3,5-diene 9α-methylcarbonate 17β-phenylcarbonate.

EXAMPLE 3C

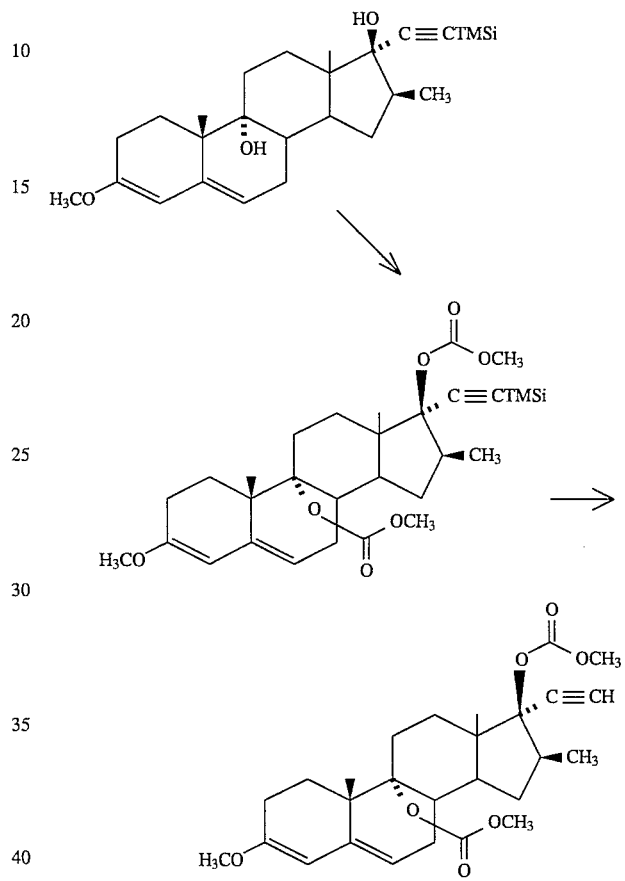

To a solution of the compound prepared in Example 2B (9.5 g) and 1,10-phenanthroline (50 mg) in 200 ml tetrahydrofuran at 0° C., n-butyl lithium was added until a dark brown color resulted (40 ml, 1.6M solution in hexane). The mixture was stirred at 0° C. for 30 minutes and 15 ml methyl chloroformate was added over a five-minute period. The mixture was then stirred overnight at room temperature. After cooling to 0° C., a cold solution of 10 g sodium bicarbonate in 100 ml water was added. The mixture was then stirred vigorously for 90 minutes followed by extraction with 200 ml ethyl acetate. The organic layer was separated, washed with brine, dried over magnesium sulfate, filtered and evaporated to afford, as an oil, 17α -trimethylsilylethynyl-9α,17β-dihydroxy-3-methoxy-16β -methylandrosta-3,5-diene, 9,17-bis(methylcarbonate).

A solution of 15 g of the compound prepared in paragraph 1 of this Example in 80 ml tetrahydrofuran was cooled to 0° C. and 30 ml of a 1M solution of tetra-n-butylammonium fluoride was added. The mixture was then stirred for 1 hour at 0° C., after which thin layer chromatography indicated a complete reaction. After quenching with 100 ml of a saturated sodium bicarbonate solution, the mixture was extracted with 1:1 ethylacetate-hexane. The organic layer was separated, washed three times with 50 ml portions of brine, and dried over magnesium sulfate and filtered. Evaporation afforded a brown oil which was chromatographed on silica. Elution with 10% ethyl acetate in hexane and 20% ethyl acetate in hexane gave 6.4 g of the product, 17α-ethynyl-9α,17β-dihydroxy-3 -methoxy-16β-methylandrosta-3,5-diene, 9,17-bis(methylcarbonate).

EXAMPLE 4A

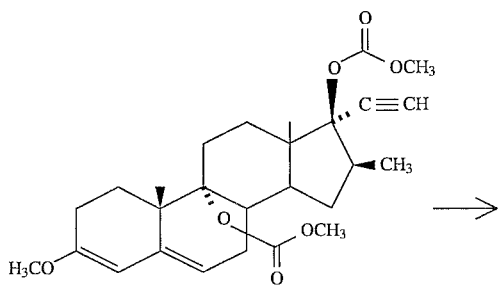

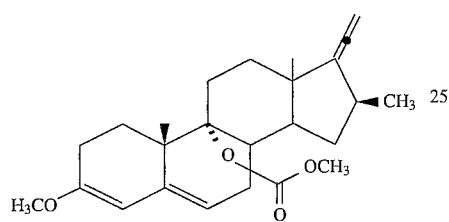

To a solution of 89 mg (0.4 mmol) Pd(OAc)₂ in dimethylsulfoxide at room temperature under nitrogen atmosphere, 170 mg (0.4 mmol) diphenylphosphinoethane was added. After 5 minutes, 1.26 g 20 (mmol) ammonium formate is added. After dissolution of the ammonium formate, 9.45 g (20 mmol) of the product prepared in Example 3A was added, and the mixture heated at 45° C. (bath temperature) for three hours.

The mixture was cooled and poured into 400 ml water, then extracted with 200 ml ethyl acetate. The organic layer was separated, washed twice with 50 ml portions of water, dried over magnesium sulfate and evaporated to give an oil. The oil was chromatographed on silica gel using ethyl acetate-hexane (1:10) to elute the desired product, 9α-hydroxy-3-methoxy-16β-methyl-17-vinylideneandrosta-3,5-diene 9α-methylcarbonate which after removal of the solvents is a white solid, (6.7 g, 84% yield).

EXAMPLE 4B

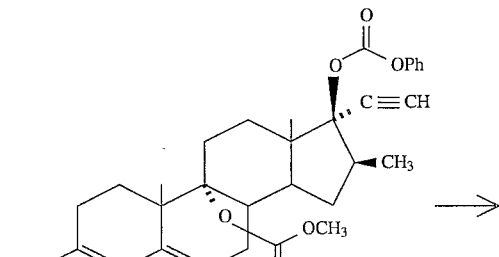

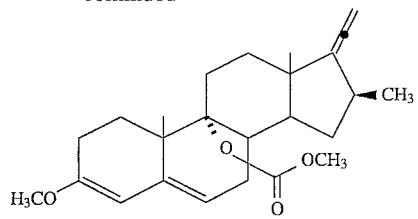

To a solution of 19 mg Pd(OAc)₂ in 7 ml dimethylsulfoxide at room temperature under nitrogen atmosphere, 34 mg diphenylphosphinoethane was added. Then, 210 mg ammonium formate was added. After ten minutes, the compound prepared in Example 3B was added in a single portion. The mixture was heated to about 45° C. for four hours. HPLC shows a yield of 86%. Workup, according to the procedure of Example 4A, afforded 9α-hydroxy-3-methoxy-16β-methyl-17 -vinylideneandrosta-3,5-diene 9α-methylcarbonate.

EXAMPLE 5

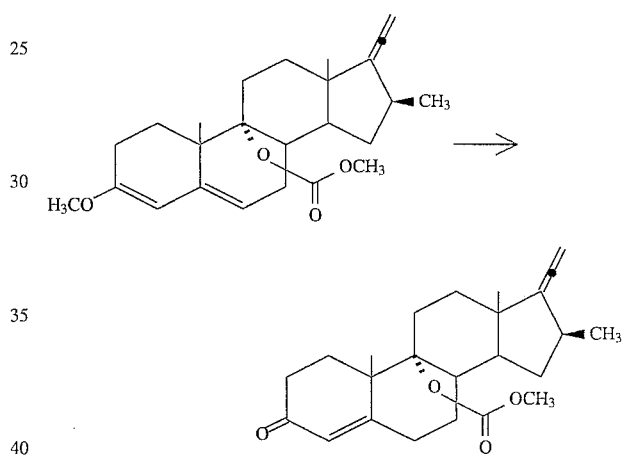

To a solution of 4 grams of the compound prepared as detailed in Example 4A or 4B in 20 ml tetrahydrofuran and 10 ml methanol at 0° C., was added 10 ml of a 1M solution of HCl in water at room temperature. The resultant mixture was stirred at 0° C. for 30 minutes and allowed to warm to room temperature. After an additional two hours of stirring at room temperature, the solution was extracted with 150 ml ethyl acetate. The organic layer was separated, washed successively with 50 ml portions of water, sodium bicarbonate and brine and dried over magnesium sulfate. Evaporation affords a residue, which was chromatographed on silica using 1:2→1:1 ethyl acetate-hexane as eluant to yield 3.0 g of the product, 9α-hydroxy-16β-methyl-17 -vinylideneandrosta-4-en-3-one 9α-methylcarbonate.

EXAMPLE 6A

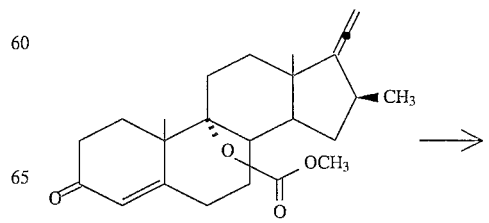

57
-continued

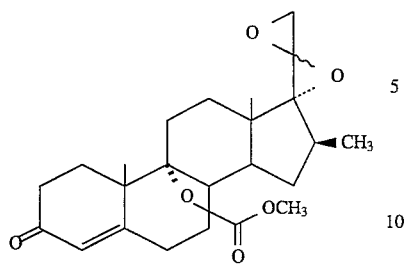

To a solution of 500 mg of the compound prepared in Example 5 in 3 ml acetone, 6 ml methylene chloride and 6 ml pH 7.0 buffer was added a solution of 4.2 g Oxone® in 16 ml water at a rate of 0.2 ml/minute. The pH was maintained at 7.6 by the addition of 5M potassium carbonate. When the Oxone® addition was complete, the resultant mixture was worked up by extraction with methylene chloride, washing with water and drying over potassium carbonate. The solvents were then evaporated to afford, as a white foamy solid, 9α-hydroxy-16β-methyl-17,20,21-bis-epoxide androsta-4-en-3-one 9α-methylcarbonate.

EXAMPLE 6B

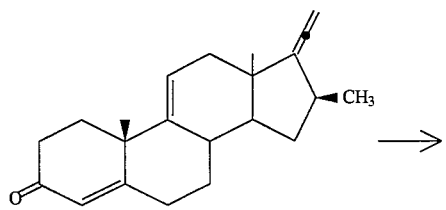

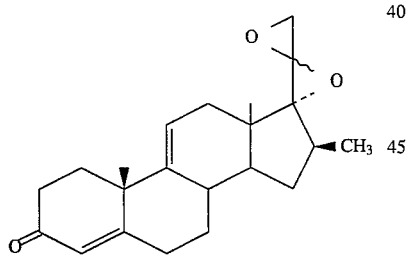

To a solution of 100 mg 16β-methyl-17-vinylideneandrosta-4,9(11)-dien-3-one in 2 ml methylene chloride, 2 ml acetone and 2 ml pH 7.5 buffer was added the Oxone® solution (1.2 g in 6 ml water, prepared as in Example 6A), at a rate of 0.2 ml/minute. The pH was maintained at 7.6 by the addition of 0.95 ml potassium carbonate solution. When the Oxone® addition was complete, the resultant mixture was worked up by extraction with methylene chloride, separation of the organic layer, and drying over potassium carbonate. Removal of the solvents afforded 17,20,21-bis-epoxide-16β-methylandrosta-4,9(11)-dien-3-one.

58
EXAMPLE 6C

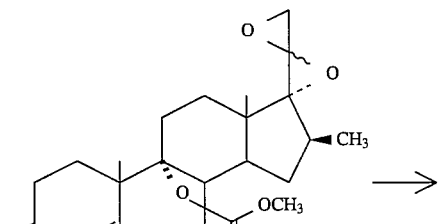

To a solution of 105 mg of 17-vinylideneandrosta-4-en-3-one in 2 ml methylene chloride and 2 ml acetone, 2 ml of a 0.5M pH 7.0 buffer was added. The mixture was then cooled to about 0° C. and Oxone® (1.2 g in 6 ml water) was added at a rate of 0.2 ml/minute, while 5M potassium carbonate solution was added to maintain the pH at about 7.6. A total of about 1.30 ml 5M potassium carbonate solution is utilized over the 35-minute reaction period. When the addition was completed, the mixture was extracted with methylene chloride, the organic layer separated and washed with water, dried over potassium carbonate and the solvents removed by evaporation to afford the resultant product, a 1:2 mixture of 17α,20,21-bis-epoxide-androsta-4-en-3-one and 17β,20,21-bis-epoxide-androsta-4-en-3-one as an oil.

EXAMPLE 7A

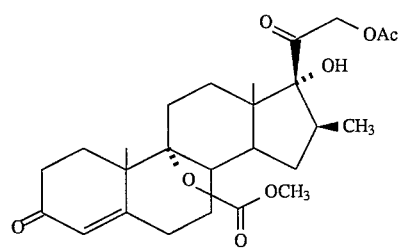

To 530 mg of the compound prepared in Example 6A in methylene chloride was added a solution of NaOAc (1 g) in water (1 ml). Then, 10 mg of tetra-n-butylammonium acetate was added, and the mixture stirred overnight. The resultant mixture was then extracted with ethyl acetate. The organic layer was separated, washed with water, dried over magnesium sulfate, filtered and the solvents removed by evaporation to afford an oily residue, which after chromatography on silica, using ethyl acetate-hexane 1:2→1:1 as eluant, afforded, as 500 mg of a white solid, the product, 21-acetoxy-9α,17α -dihydroxy-16β-methylpregna-4-ene-3, 20-dione 9α-methylcarbonate.

EXAMPLE 7B

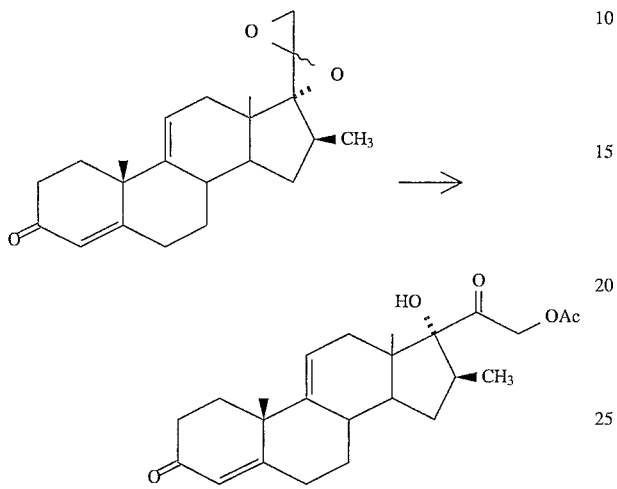

The compound prepared in Example 6B was dissolved in 2 ml methylene chloride and 2 ml water and treated with 500 mg sodium acetate and tetra-n-butylammonium acetate. After stirring for about 90 minutes, the reaction mixture was extracted with 20 ml ethylacetate. After separation, the organic layer was washed twice with water, dried over magnesium sulfate and the solvents removed to afford 21-acetoxy-17-hydroxy-16β -methylpregna-4,9(11)diene-3, 20-dione.

EXAMPLE 7C

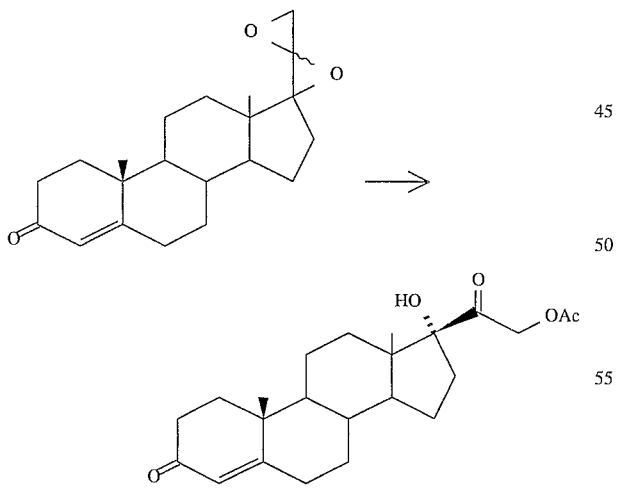

To the product prepared above in Example 6C in a solution of 2 ml methylene chloride was added a solution of 1 gram sodium acetate in 2 ml water, followed by 20 mg of tetra-n-butylammonium acetate. The resultant mixture was stirred for 3 hours and then extracted with ethyl acetate. The organic layer was separated, washed successively with water and brine, dried over magnesium sulfate and the solvents removed by evaporation to give, as an oil, 21-acetoxy-17α-hydroxypregna-4-ene-3,20-dione and its corresponding isomer, 21-acetoxy-17β -hydroxypregna-4-ene-3,20-dione.

EXAMPLE 8

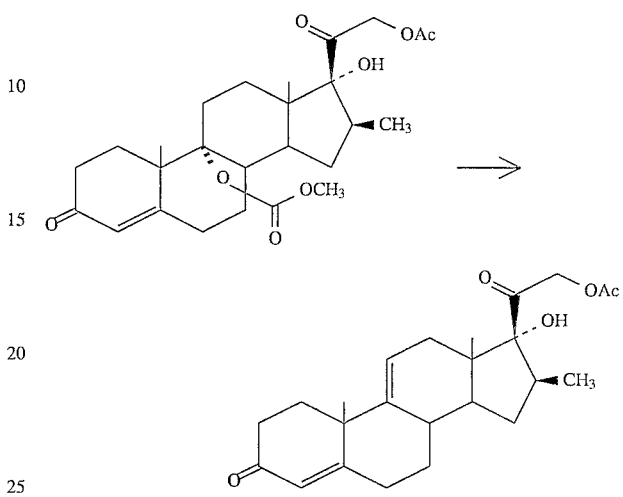

To a solution of 6.0 mg of the compound prepared in Example 7A in 1 ml methylene chloride was added 91.7 mg trifluoroacetic acid. After 30 minutes, 150 mg triethylamine was added, and the solution diluted to 10 ml with acetonitrile. HPLC indicated a yield of 100% of the product, 21-acetoxy-17α-hydroxy-16β-methylpregna- 4,9(11)-diene-3,20-dione.

Alternately, 1 ml trifluoroacetic acid was added to 200 mg of the compound prepared in Example 7A in 5 ml methylene chloride at room temperature. After 30 minutes of stirring, the solution was cooled to room temperature and 20 ml water is added. The resultant mixture was extracted twice with 20 ml portions of ethyl acetate and the organic layer subsequently washed with 20 ml portions of water and sodium bicarbonate. After drying over magnesium sulfate and filtering, the solvents were evaporated to afford 160 mg of the product 21-acetoxy-17α-hydroxy-16β-methylpregna-4,9(11)diene- 3,20-dione.

EXAMPLE 9

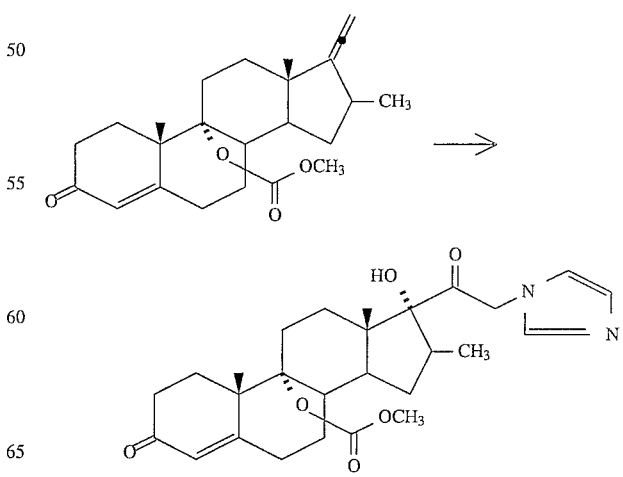

Substantial repetition of the procedure detailed in Example 6A utilizing 30 mg 9α-hydroxy-16β-methyl-17-vinylideneandrosta-4-en-3-one 9α-methylcarbonate afforded 9α-hydroxy-16β-methyl-17,20,21-bis-epoxide-androsta- 4-en-3-one 9α-methylcarbonate which was then further reacted with 10 mg imidazole into chloroform to yield 21-imidazolyl-9α,17α-dihydroxy-16β-methylpregna-4-ene-3,20-dione 9α-methylcarbonate.

EXAMPLE 10

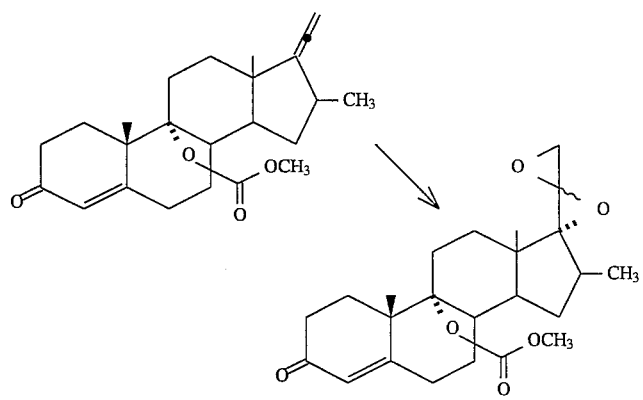

Substantial repetition of the procedure detailed in Example 6A utilizing 150 mg 9α-hydroxy-16β-methyl-17-vinylideneandrosta-4-en-3-one 9α-methylcarbonate afforded 9α-hydroxy-16β-methyl-17,20,21-bis-epoxide-androsta- 4-en-3-one 9α-methylcarbonate which was then dissolved in methylene chloride and further reacted with 100 mg sodium bromide and 10 mg tetra-n-butylammonium bromide to yield 21-bromo-9α,17α-dihydroxy-16β-methyl-pregna-4-ene-3,20-dione 9α-methylcarbonate.

EXAMPLE 11

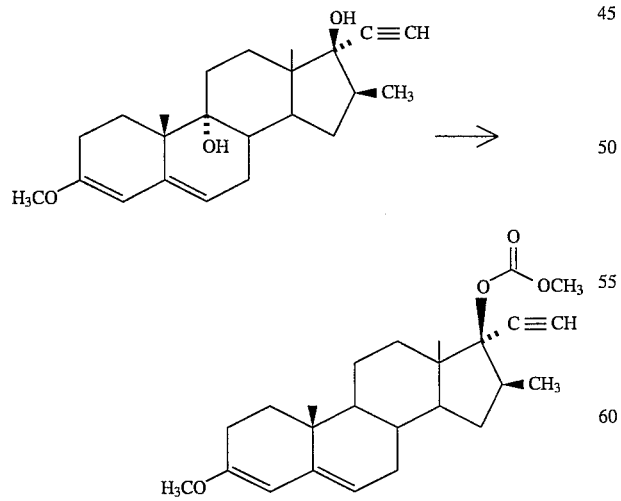

To a solution of 1.1 g phenol in 10 ml tetrahydrofuran, cooled to 0°–5° C. was added sodium hydride (60%, 950 mg) portionwise. Then, 0.8 ml methylchloroformate was added dropwise and the resulting mixture allowed to warm to room temperature. To this mixture was added 0.5 g of 17α-ethynyl-9α,17β-dihydroxy-3-methoxy-16β -methylandrosta-3,5-diene and the mixture stirred overnight. Chromatography afforded 17α-ethynyl-9α,17β -dihydroxy-3-methoxy-16β-methylandrosta-3,5-diene 17β -methylcarbonate.

What is claimed is:

1. A process for the preparation of steroid intermediates of the formula

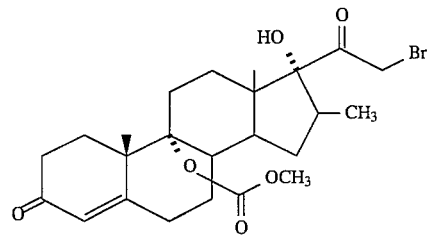

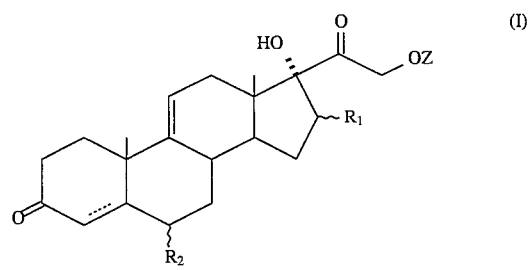

wherein

Z is an acyl group;

$R_1$ is a hydrogen, α- or β-methyl, hydroxy, or a lower alkoxy group;

$R_2$ is hydrogen, fluoro, chloro or lower alkyl; and the dotted line represents an optional double bond; which comprises:

a. optionally contacting a 9α-hydroxy steroid of the formula

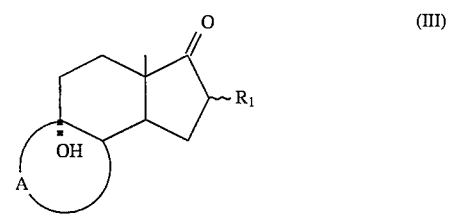

wherein $R_1$ is as hereinbefore defined and

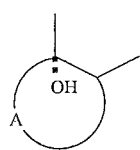

represents i) an enol ether of the formula:

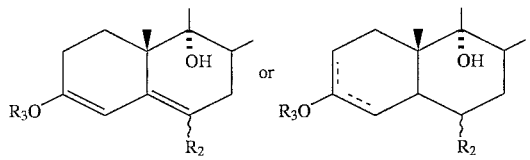

wherein $R_3$ is a lower alkyl or a trisubstituted silyl group wherein the silyl substituents are independently lower alkyl, phenyl or phenylalkyl; the dashed line represents a double bond present in one or the other position; and $R_2$ is as hereinbefore defined;

ii) a ketal of the formula:

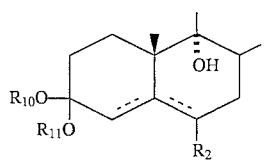

wherein $R_{10}$ and $R_{11}$ independently are lower alkyl groups, optionally connected together to form a five or six membered ring; the dashed lines represent an optional bond present in either the A or B ring; and $R_2$ is as hereinbefore defined; or iii) an enamine of the formula

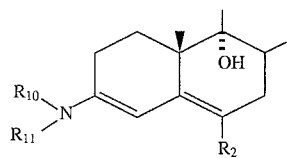

wherein $R_2$, $R_{10}$ and $R_{11}$ are as hereinbefore defined with the proviso that the optional six membered ring may optionally contain an oxygen or nitrogen atom;

with either
1) excess base and a trisubstituted silylchloride;
2) a lower alkyl, vinyl or phenyl haloformate; and
3) a lower alkanol;

or
1) excess base;
2) a lower alkyl, vinyl or phenyl haloformate; and
3) an alkoxide to afford the C-9 carbonate of the formula a)

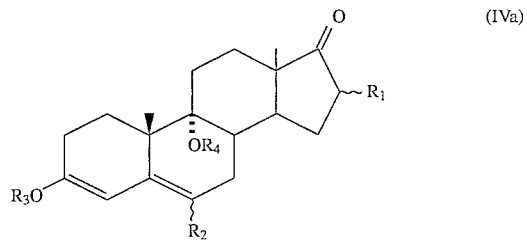 (IVa)

b)

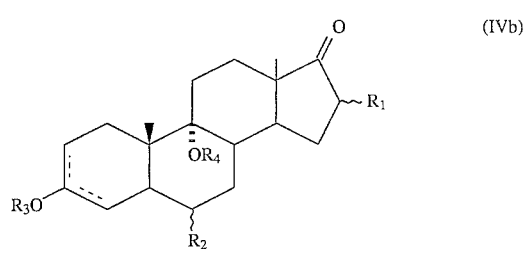 (IVb)

c)

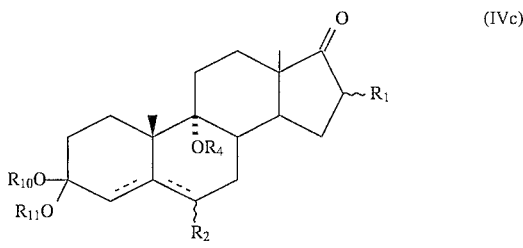 (IVc)

or d)

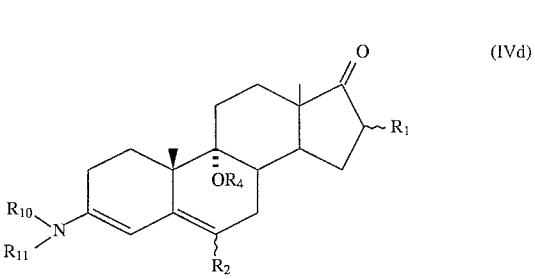 (IVd)

wherein $R_4$ is a lower alkyl, vinyl or phenyl carbonate group, and $R_1$, $R_2$, $R_3$, $R_{10}$ and $R_{11}$ are as hereinbefore defined;

b. contacting the resultant C-9 carbonate of step a or the 9α-hydroxy starting material of formula III with lithium acetylide or lithium trimethylsilyl acetylide optionally in the presence of LiX wherein X is a chloro, bromo or perchlorate ion, to afford the C-17 ethynyl compound of the formula

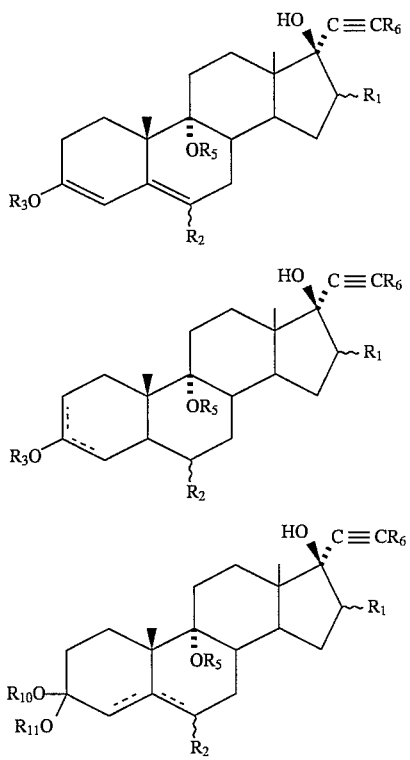

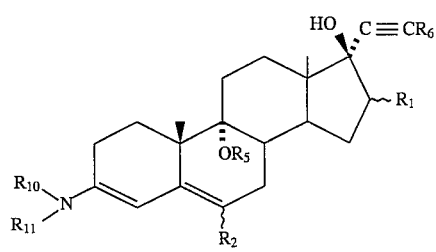

wherein $R_5$ is hydrogen, a lower alkyl carbonate, a vinyl carbonate or a phenyl carbonate group, $R_6$ is hydrogen or a trimethylsilyl group; $R_1$, $R_2$, $R_3$, $R_{10}$, $R_{11}$ and the dashed and dotted lines are as hereinbefore defined;

c. esterifying the resulting C-17 hydroxyl compound of step b with
1) catalytic phenoxide formed in in situ with a metal hydride and a phenol; and
2) a diarylcarbonate of the formula

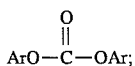

or an alkylaryl carbonate of the formula

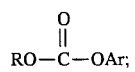

or a diarylcarboxylate of the formula

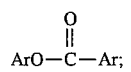

or an arylalkylcarboxylate of the formula

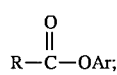

wherein R is a lower alkyl group and Ar is an aryl group; and
3) a metal hydride; in an aprotic solvent;
to afford the C-17 ester of the formula a) 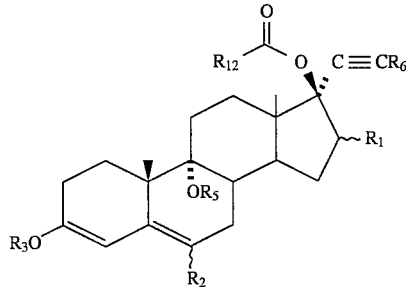

b) 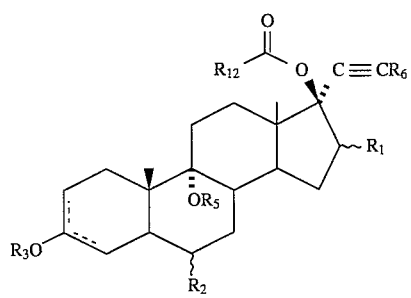

c) 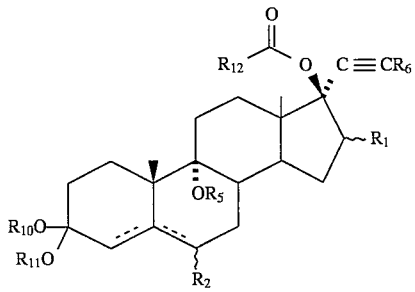

or d) 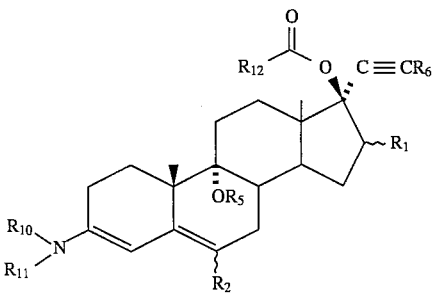

wherein $R_{12}$ is a lower alkyl, aryl, lower alkoxy or aryloxy group and $R_1$, $R_2$, $R_3$, $R_5$, $R_{10}$, $R_{11}$ and the dashed and dotted lines are as hereinbefore defined; and in the case wherein $R_6$ is a trisubstituted silyl group, removal of that group by a conventional desilylation method;

d. contacting the resulting C-17 ester of step c with one of the following reducing agents:

1. formic acid or its salts;
2. a samarium (II) salt;
3. a transition metal;

and a palladium catalyst containing a phosphine or phosphite ligand, to afford the 17-allene of the formula a)

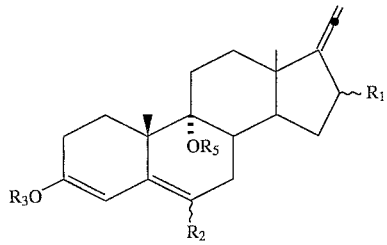

(VIIa)

b)

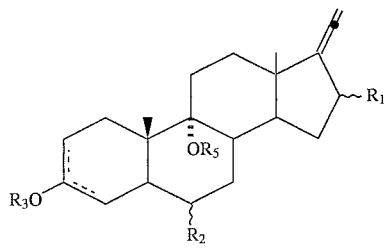

(VIIb)

c)

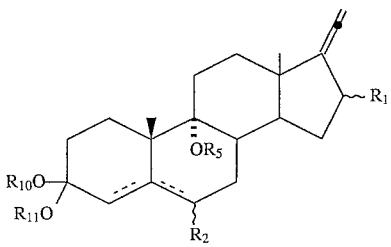

(VIIc)

or d)

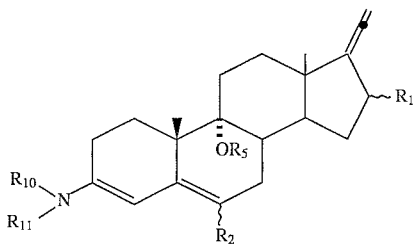

(VIId)

wherein $R_1$, $R_2$, $R_3$, $R_5$, $R_{10}$, $R_{11}$ and the dashed and dotted lines are as hereinbefore defined;

e. treatment of the resulting 17-allene of step d with an aqueous strong acid to afford the 3-one of the formula

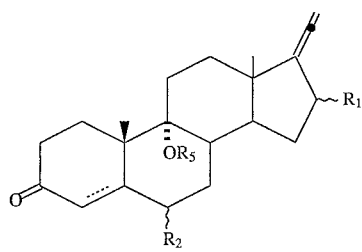

(VIII)

wherein $R_1$, $R_2$, $R_5$ and the dotted line are as hereinbefore defined;

f. oxidizing the resulting 3-one of step e with a dialkyl dioxirane to afford the compound of the formula

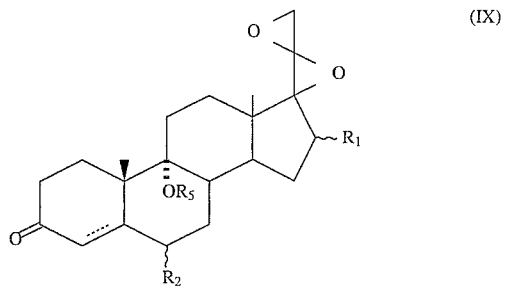

(IX)

wherein $R_1$, $R_2$, $R_5$ and the dotted line are as hereinabove defined;

g. treatment of the compound of step f with an alkali metal salt of a carboxylic acid under phase-transfer conditions to afford the compound of the formula

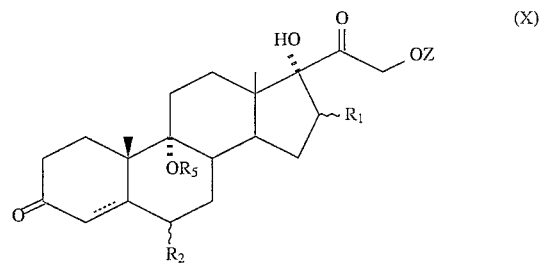

(X)

wherein Z is an acyl group, $R_1$, $R_2$, $R_5$, and the dotted line are as hereinbefore defined; and h. treatment of the compound of step g with a strong acid to afford the $\Delta 9,11$ steroid of formula I.

2. The process of claim 1 wherein the compound of step f is treated with a halide to afford the 21-halo compound of the formula

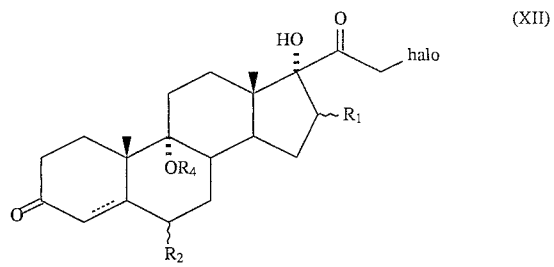

(XII)

wherein halo is chloro, bromo or iodo, and $R_1$, $R_2$ and $R_4$ are as hereinbefore defined; and then reacted according to the reaction conditions of step g and step h to afford the $\Delta 9,11$ steroid of formula I.

3. The process of claim 1 wherein a C-9 carbonate of step a is utilized for step b.

4. The process of claim 1 wherein a 9-hydroxy compound of formula III is utilized directly in step b.

5. The process of claim 1 wherein the reagents utilized for step a are:

1) excess base and a trialkylsilyl chloride
2) a lower alkyl, vinyl or phenyl chloroformate; and
3) a lower alkanol.

6. The process of claim 1 wherein the reagents utilized for step a are:

1) excess base;
2) a lower alkyl, vinyl or phenyl chloroformate; and
3) alkoxide.

7. The process of claim 1 wherein the 9-carbonate is utilized along with about 2 equivalents of lithium ion and about 2 equivalents of lithium acetylide in step b.

8. The process of claim 1 wherein a diarylcarbonate of the formula

or alkylaryl carbonate of the formula

wherein R is a lower alkyl group and Ar is an aryl group is utilized for step c.

9. The process of claim 1 wherein ammonium formate, palladium acetate and diphenylphosphinoethane are utilized for the conduct of step d.

10. The process of claim 1 wherein aqueous hydrochloric acid is utilized for the conduct of step e.

11. The process of claim 1 wherein the dimethyl dioxirane is produced in situ for the conduct of step f.

12. The process of claim 1 wherein sodium acetate and tetra-n-ammonium acetate are utilized for the conduct of step g.

13. The process of claim 1 wherein trifluoroacetic acid is utilized for the conduct of step h.

14. A process for the preparation of steroid intermediates of the formula

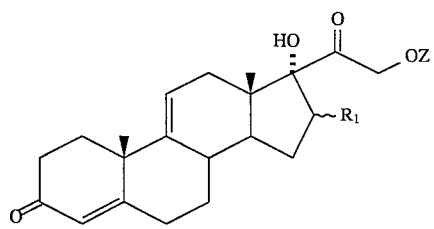

wherein Z is an acyl group;

$R_1$ is a hydrogen, $\alpha$- or $\beta$-methyl, hydroxy, or a lower alkoxy group; which comprises:

a) contacting a 9$\alpha$-hydroxy steroid of the formula

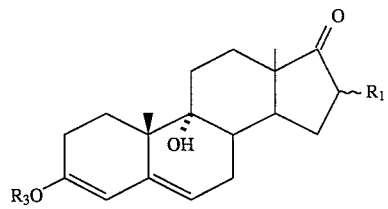

wherein $R_3$ is lower alkyl and $R_1$ is as hereinbefore defined; with 1) excess base and a trialkylsilyl chloride
2) a lower alkyl chloroformate; and
3) a lower alkanol; or
1) excess base;
2) a lower alkyl chloroformate; and
3) an alkoxide to afford the C-9 carbonate of the formula

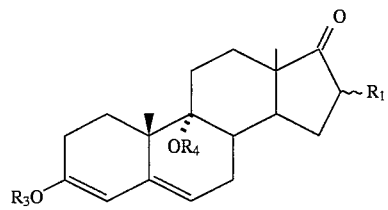

wherein $R_4$ is lower alkyl, and $R_1$ and $R_3$ are as hereinbefore defined, b. contacting the resultant C-9 carbonate of step a with about 2 equivalents of lithium acetylide in the presence of LiX wherein X is a chloro, bromo or perchlorate ion to afford the C-17 ethynyl compound of the formula

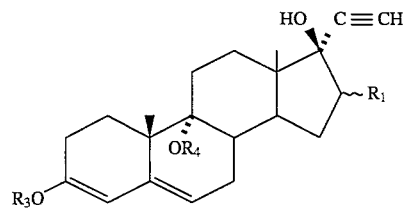

wherein $R_1$, $R_3$ and $R_4$ are as hereinbefore defined;

c. esterifying the resulting C-17 hydroxyl compound of step b with
1. catalytic phenoxide formed in situ with a metal hydride and a phenol; and
2. a diarylcarbonate of the formula

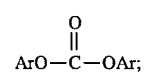

or an alkylaryl carbonate of the formula

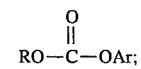

or a diarylcarboxylate of the formula

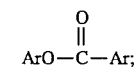

or an arylalkylcarboxylate of the formula

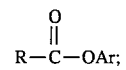

wherein R is a lower alkyl group and Ar is an aryl group; and
3. a metal hydride; in an aprotic solvent;
to afford the C-17 ester of the formula

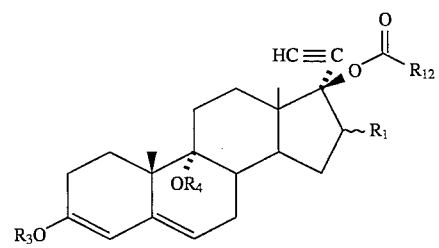

wherein $R_{12}$ is a lower alkyl, aryl, lower alkoxy or aryl oxy group and $R_1$, $R_3$ and $R_4$ are as hereinbefore defined;

d. contacting the resulting C-17 ester of step c with one of the following reducing agents:
1. formic acid or its salts;
2. a samarium (II) salt;
3. a transition metal;

and a palladium catalyst containing a phosphine or phospite ligand, to afford the 17-allene of the formula

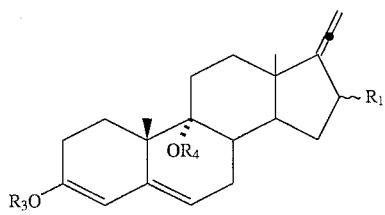

(XVII)

wherein $R_1$, $R_3$ and $R_4$ are as hereinbefore defined;

e. treatment of the resulting 17-allene of step d with an aqueous strong acid to afford the 3-one of the formula

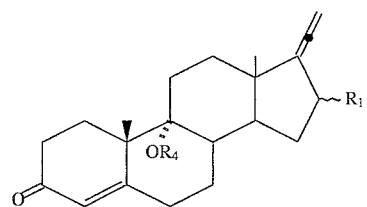

(XVIII)

f) oxidizing the resulting 3-one of step e with a dialkyl dioxirane to afford the compound of the formula

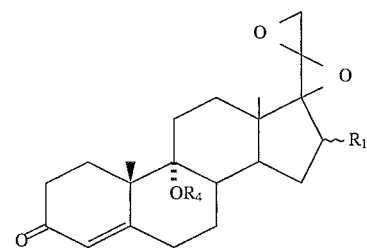

(XIX)

wherein $R_1$ and $R_4$ are as hereinabove defined;

g) treatment of the compound of step f with an alkali metal salt of a carboxylic acid under phase-transfer conditions to afford the compound of the formula

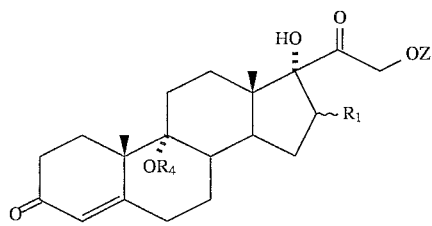

(XX)

wherein $R_1$, $R_4$ and Z are as hereinbefore defined; and h) treatment of the compound of step g with a mineral or strong organic acid to afford the Δ9,11 steroid of formula II.

15. A process for the preparation of compounds of the formula I

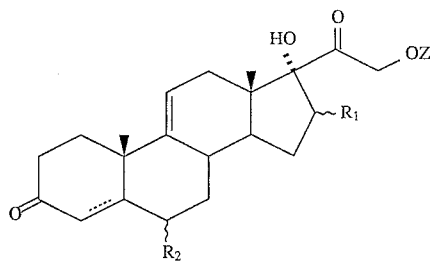

wherein $R_1$ is a hydrogen, α or β-methyl, hydroxy or lower alkoxy; $R_2$ is hydrogen, fluoro, chloro or lower alkyl; Z is an acyl group; and the dotted line represents an optional double bond; which comprises:

a) contacting a 17-allene of the formula

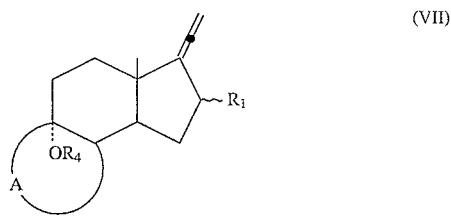

(VII)

wherein $R_4$ is a lower alkyl, vinyl or phenyl carbonate group, $R_1$ is as hereinbefore defined; and is i) an enol ether of the formula:

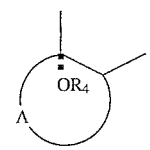

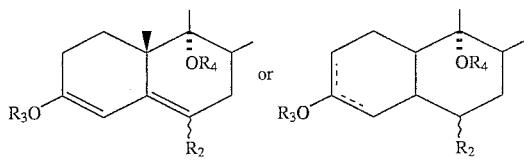

wherein $R_3$ is a lower alkyl or a trisubstituted silyl group wherein the silyl substituents are independently lower alkyl, phenyl or phenylalkyl; the dashed line represents a double bond present in one or the other position; and $R_2$ is as hereinbefore defined;

ii) a ketal of the formula:

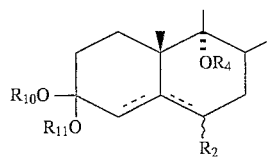

wherein $R_{10}$ and $R_{11}$ independently are lower alkyl groups, optionally connected together to form a ring which optionally may contain an oxygen or nitrogen atom; the dashed lines represent an optional bond present in either the A or B ring; and $R_2$ is as hereinbefore defined; or iii) an enamine of the formula

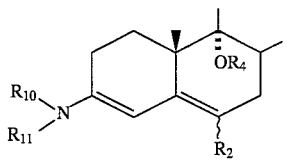

wherein $R_2$, $R_{10}$ and $R_{11}$ are as hereinbefore defined; with an aqueous strong acid to afford the 3-one of the formula

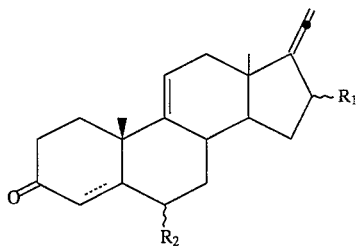

(XXI)

wherein $R_1$, $R_2$ and the dotted line are as hereinbefore defined;

b. oxidizing the resultant 3-one of step b with a dialkyl dioxirane to afford the compound of the formula

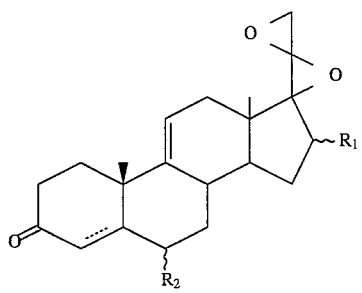

(XXII)

wherein $R_1$, $R_2$, and the dotted line are as hereinbefore defined;

c. treatment of the compound produced in step b with an alkali metal salt of a carboxylic acid under phase transfer conditions to afford the desired compound of formula I.

16. A process for the preparation of compounds of the formula

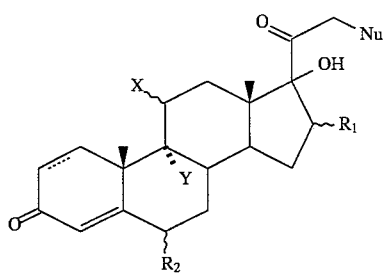

(XXVI)

wherein Nu is —OR, —SR,

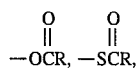

halogen, —$N_3$,

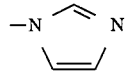

—NRR, —SCN, —CN, —$SO_2R$, —N(R)NRR, —N(R)OR or —ONRR; wherein R is independently hydrogen, lower alkyl, cycloalkyl, alkenyl, aryl, optionally substituted by lower alkyl, halogen or nitro groups;

$R_1$ is a hydrogen, α- or β-methyl hydroxy or a lower alkoxy group;

$R_2$ is hydrogen, fluoro, chloro or lower alkyl;

X is hydrogen, hydroxy or $OR_{13}$;

Y is hydrogen, or when X is hydrogen and there is no 1,2 double bond present, $OR_5$, wherein $R_5$ is hydrogen or a lower alkyl, vinyl or phenylcarbonate group; or X and Y taken together form a 9,11 double bond; $R_{13}$ is a conventional hydroxy protecting group; and the dotted lines represent an optional double bond;

which comprises reacting a compound of the formula

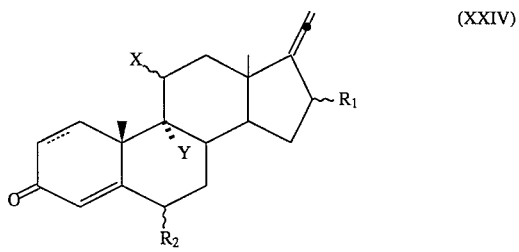

(XXIV)

wherein $R_1$, $R_2$, X, Y and the dotted lines are as hereinbefore defined;

with dimethyldioxirane generated in situ to afford the bis-epoxide compound of the formula

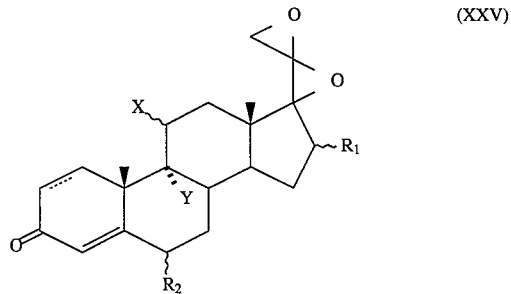

(XXV)

wherein $R_1$, $R_2$, X and Y and the dotted lines are as hereinbefore defined; which is then reacted with a nucleophilic reagent to afford the desired compound of formula XXVI.

17. A process for the preparation of Δ9(11) enes of the formula

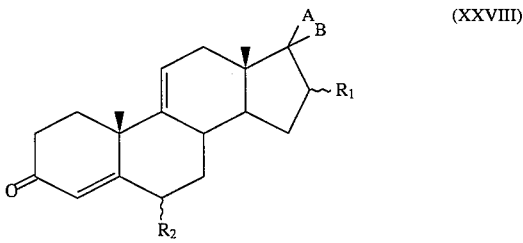

(XXVIII)

wherein A and B together are keto, ketal, allene;

or =CHCH$_2$OR$_{13}$, or

A is hydrogen, lower alkyl, lower alkenyl, lower alkynyl aryl or alkylaryl; —CN,

or —COCH$_2$W;

B is hydrogen, OH, OR$_{13}$, or together with carbon 16 forms a 16,17-double bond or a 16,17-epoxide;

R$_1$ is hydrogen, α- or β-methyl, hydroxy or lower alkoxy;

R$_2$ is hydrogen, fluoro, chloro or lower alkyl;

R$_{13}$ is a conventional hydroxyl protecting group;

W is hydrogen, lower alkyl, lower alkenyl, lower alkynyl, aryl or alkylaryl; —OR, —SR,

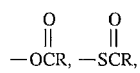

halogen, —N$_3$,

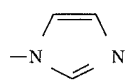

—NRR, —SCN, —CN, —SO$_2$R, —N(R)NRR, —N(R)OR or —ONRR; R is independently hydrogen, lower alkyl, cycloalkyl, alkenyl, aryl, optionally substituted by lower alkyl, halogen or nitro groups;

which comprises treatment of a compound of formulae XXVIIa or XXVIIb

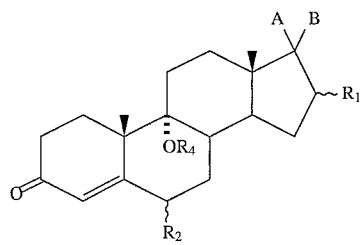

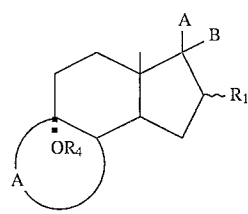

wherein R$_4$ is a lower alkyl, vinyl or phenyl carbonate group;

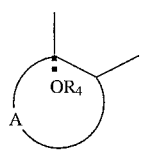

represents i) an enol ether of the formula:

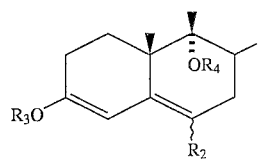

or

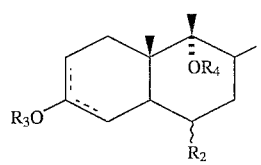

wherein R$_3$ is a lower alkyl or a trisubstituted silyl group wherein the silyl substituents are independently lower alkyl, phenyl or phenylalkyl; the dashed line represents a double bond present in one or the other position; and R$_2$ and R$_4$ are as hereinbefore defined;

ii) a ketal of the formula:

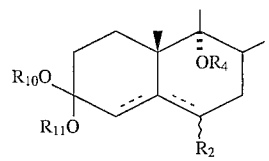

wherein R$_{10}$ and R$_{11}$ independently are lower alkyl groups, optionally connected together to form a ring which optionally may contain an oxygen or nitrogen atom; the dashed lines represent an optional bond present in either the A or B ring; R$_4$ is as hereinbefore defined; and iii) an enamine of the formula

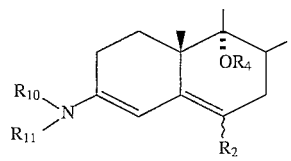

wherein R$_2$, R$_4$, R$_{10}$ and R$_{11}$ are as hereinbefore defined;

A, B and R$_1$ are as hereinbefore defined, with a strong acid in the case of compounds XXVIIA or an aqueous strong acid for compounds XXVIIa or XXVIIb to generate the 9(11) enes of formula XXVIII.

18. Compounds of the formula

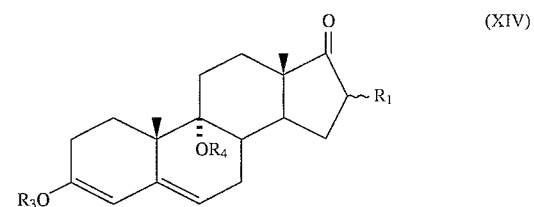

wherein R$_1$ is a hydrogen, α- or β-methyl, hydroxy, or a lower alkoxy group;

R$_3$ is a lower alkyl or a trisubstituted silyl group wherein the silyl substituents are independently lower alkyl, phenyl or phenylalkyl; and R$_4$ is a lower alkyl, vinyl or phenyl carbonate group.

19. The compound according to claim 18 which is 9α-hydroxy-3-methoxy-16β-methylandrost-3,5-diene-17-one 9α-methylcarbonate.

20. Compounds of the formula

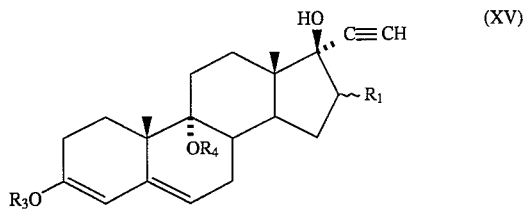

wherein $R_1$ is hydrogen, α- or β-methyl, hydroxy, or a lower alkoxy group;

$R_3$ is a lower alkyl or a trisubstituted silyl group wherein the silyl substituents are independently lower alkyl, phenyl or phenylalkyl; and $R_4$ is a lower alkyl, vinyl or phenyl carbonate group.

21. The compound according to claim 20 which is 17α-ethynyl-9α,17β-dihydroxy-3-methoxy-16β-methyland-rosta-3,5-diene 9-methylcarbonate.

22. Compounds of the formula

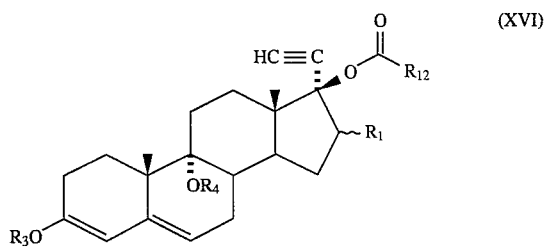

wherein $R_1$ is hydrogen, α- or β-methyl, hydroxy, or a lower alkoxy group;

$R_3$ is a lower alkyl or a trisubstituted silyl group wherein the silyl substituents are independently lower alkyl, phenyl or phenylalkyl;

$R_4$ is a lower alkyl, vinyl or phenyl carbonate group; and $R_{12}$ is a lower alkyl, aryl, lower alkoxy or aryloxy group.

23. The compound according to claim 22 which is 17α-ethynyl-9α,17β-dihydroxy-3-methoxy-16β-methyland-rosta-3,5-diene, 9,17-bis(methylcarbonate).

24. The compound according to claim 22 which is 17α-ethynyl-9α,17β-dihydroxy-3-methoxy-16β-methyland-rosta-3,5-diene 9α-methylcarbonate 17β-phenylcarbonate.

25. Compounds of the formula

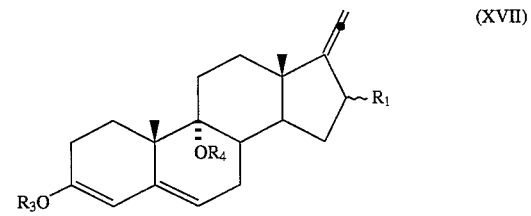

wherein $R_1$ is hydrogen, α- or β-methyl, hydroxy, or a lower alkoxy group;

$R_3$ is a lower alkyl or a trisubstituted silyl group wherein the silyl substituents are independently lower alkyl, phenyl or phenylalkyl; and $R_4$ is a lower alkyl, vinyl or phenyl carbonate group.

26. The compound according to claim 25 which is 9α-hydroxy-3-methoxy-16β-methyl-17-vinylideneandrosta-3,5-diene 9α-methylcarbonate.

27. Compounds of the formula

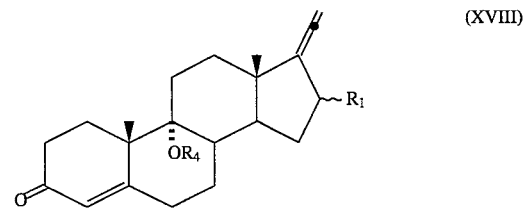

wherein $R_1$ is hydrogen, α- or β-methyl, hydroxy, or a lower alkoxy group; and $R_4$ is a lower alkyl, vinyl or phenyl carbonate group.

28. The compound according to claim 27 which is 9α-hydroxy-16β-methyl-17-vinylideneandrosta-4-en-3-one 9α-methylcarbonate.

29. Compounds of the formula

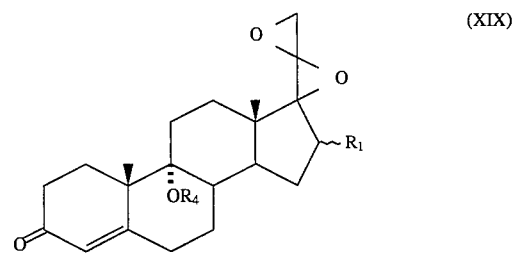

wherein $R_1$ is hydrogen, α- or β-methyl, hydroxy, or a lower alkoxy group; and $R_4$ is a lower alkyl, vinyl or phenyl carbonate group.

30. The compound according to claim 29 which is 9α-hydroxy-16β-methyl-17,20,21-bis-epoxide-androsta-4-en-3-one 9α-methylcarbonate.

31. Compounds of the formula

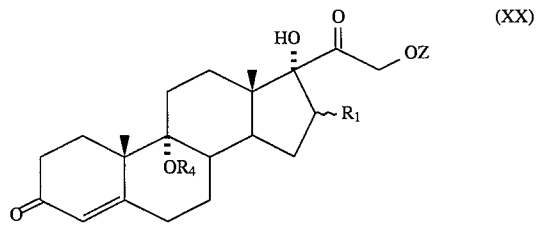

wherein $R_1$ is hydrogen, α- or β-methyl, hydroxy, or a lower alkoxy group;

$R_4$ is a lower alkyl, vinyl or phenyl carbonate group; and

Z is an acyl group.

32. The compound according to claim 31 which is 21-acetoxy-9α,17β-dihydroxy-16β-methylpregna-4-ene-3,20-dione 9α-methylcarbonate.

33. Compounds of the formula

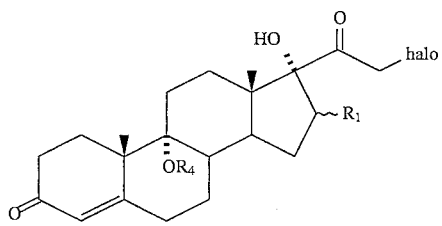 (XIIb)
wherein halo is chloro, bromo or iodo;
R$_1$ is hydrogen, α- or β-methyl, hydroxy, or a lower alkoxy group; and
R$_4$ is a lower alkyl, vinyl or phenyl carbonate group.
34. The compound according to claim 33 which is 21-bromo-9α,17β-dihydroxy-16β-methylpregna-4-ene-3,20-dione 9α-methylcarbonate.
35. The compound which is 21-imidazolyl-9α,17β-dihydroxy-16β-methylpregna-4-ene-3,20-dione 9α-methylcarbonate.
* * * * *